United States Patent
Juric et al.

(10) Patent No.: US 10,846,288 B2
(45) Date of Patent: Nov. 24, 2020

(54) COMPUTER IMPLEMENTED METHOD FOR EXTRACTING AND REASONING WITH MEANING FROM TEXT

(71) Applicant: Babylon Partners Limited, London (GB)

(72) Inventors: Damir Juric, London (GB); Georgios Stoilos, London (GB); Szymon Wartak, London (GB); Mohammad Khodadadi, London (GB)

(73) Assignee: Babylon Partners Limited, London (GB)

( * ) Notice: Subject to any disclaimer, the term of this patent is extended or adjusted under 35 U.S.C. 154(b) by 133 days.

(21) Appl. No.: 16/025,539

(22) Filed: Jul. 2, 2018

(65) Prior Publication Data

US 2020/0004832 A1 Jan. 2, 2020

(51) Int. Cl.
*G06F 16/00* (2019.01)
*G06F 16/2452* (2019.01)
(Continued)

(52) U.S. Cl.
CPC ...... *G06F 16/24522* (2019.01); *G06F 40/284* (2020.01); *G06N 5/04* (2013.01); *G16H 10/00* (2018.01); *G16H 50/00* (2018.01)

(58) Field of Classification Search
CPC ........... G06F 3/00; G06F 16/00; G06F 16/245
See application file for complete search history.

(56) References Cited

U.S. PATENT DOCUMENTS

| | | | |
|---|---|---|---|
| 9,336,269 B1 * | 5/2016 | Smith | G06F 16/245 |
| 2014/0237356 A1 * | 8/2014 | Durga | G06F 3/0237 |
| | | | 715/256 |

(Continued)

FOREIGN PATENT DOCUMENTS

| | | |
|---|---|---|
| CN | 107 451 153 | 12/2017 |
| CN | 107 885 786 | 4/2018 |
| WO | 2012067586 | 5/2012 |

OTHER PUBLICATIONS

Arora, S., Liang, Y., Ma, T.: A simple but tough-to-beat baseline for sentence embeddings. In: Proceedings of the 5th International Conference on Learning Representations (ICLR). pp. 1-14 (2017).

(Continued)

*Primary Examiner* — Shreyans A Patel
(74) *Attorney, Agent, or Firm* — McDermott Will & Emery LLP

(57) ABSTRACT

A text processing method for improving the accuracy of a response to a query directed to a system comprising concepts and relations defined by a knowledge base, wherein the method comprises:

(i) producing a dependency tree from the query, wherein the dependency tree has at least one branch containing nodes and at least one connection between those nodes, wherein each node has a node label which corresponds to a term within the query, and wherein each connection has a label which corresponds to the linguistic relationship between terms within the query;

(ii) from the dependency tree, generating a query concept using concepts and relations defined by the knowledge base;

(iii) checking if the query concept has a subsumption relationship with a candidate concept retrieved from the system, and if no subsumption relationship is initially identified, optimising the dependency tree by changing the nodes, followed by repeating steps (ii) and (iii);

and wherein the query concept and the candidate concept comprise at least one atomic concept.

22 Claims, 13 Drawing Sheets

(51) Int. Cl.
*G16H 50/00* (2018.01)
*G16H 10/00* (2018.01)
*G06F 40/284* (2020.01)
*G06N 5/04* (2006.01)

(56) References Cited

U.S. PATENT DOCUMENTS

2014/0324750 A1* 10/2014 Christophe ............ G06N 5/022 706/46
2015/0310073 A1* 10/2015 Chakrabarti ........ G06F 16/2465 707/722
2018/0181648 A1* 6/2018 Chen ................... G06F 16/9027

OTHER PUBLICATIONS

Auer, S., Bizer, C., Kobilarov, G., Lehmann, J., Cyganiak, R., Ives, Z.: DBpedia: A nucleus for a web of open data. In: Proc. of the 6th Int. Semantic Web and 2nd Asian Semantic Web Conference. pp. 722-735 (2007).

Fernandez-Breis, J.T., Iannone, L., Palmisano, I., Rector, A.L, Stevens, R.: Enriching the gene ontology via the dissection of labels using the ontology pre-processor language. In: Proceedings of the 17th International Conference on Knowledge Engineering and Management by the Masses. pp. 59-73. Springer-Verlag (2010).

Hachey, B., Radford, W., Nothman, J., Honnibal, M., Curran, J.R.: Evaluating entity linking with Wikipedia. Artificial Intelligence 194, 130-150 (2013).

Kao, H., Tang, K., Chang, E.Y.: Context-aware symptom checking for disease diagnosis using hierarchical reinforcement learning. In: Proceedings of the Thirty-Second AAAI Conference on Artificial Intelligence (AAAI) (2018).

Milward, D., Beveridge, M.: Ontology-based dialogue systems. In: 3rd Workshop on Knowledge and reasoning in practical dialogue systems (2003).

Nickel, M., Murphy, K., Tresp, V., Gabrilovich, E.: A review of relational machine learning for knowledge graphs. Proceedings of the IEEE 104(1), 11-33 (2016).

Oramas, S., Ostuni, V.C., Noia, T.D., Sega, X., Sciascio, E.D.: Sound and music recommendation with knowledge graphs. ACM Trans. Intell. Syst. Technol. 8(2), 21:1-21:21 (2016).

Pacheco, E.J., Stenzhorn, H., Nohama, P., Paetzold, J., Schulz, S.: Detecting under specification in SNOMED CT concept definitions through natural language processing. In: Proceedings of the American Medical Informatics Association Annual Symposium (2009).

Papadakos, P., Armenatzoglou, N., Kopidaki, S., Tzitzikas, Y.: On exploiting static and dynamically mined metadata for exploratory web searching. Knowledge and Information Systems 30(3), 493-525 (2012).

Qarabaqi, B., Riedewald, M.: User-driven refinement of imprecise queries. In: IEEE 30th International Conference on Data Engineering ICDE. pp. 916-927 (2014).

Razzaki, S., Baker, A., Perov, Y., Middleton, K, Baxter, J., Mullarkey, D., Sangar, D., Taliercio, M., Butt, M., Majeed, A., DoRosario, A., Mahoney, M., Johri, S.: A comparative study of artificial intelligence and human doctors for the purpose of triage and diagnosis. CoRR abs/1806.10698 (2018).

Semigran, H.L., Linder, J.A., Gidengil, C., Mehrotra, A.: Evaluation of symptom checkers for self diagnosis and triage: audit study. The BMJ 351 (2015).

Stoilos, G., Geleta, D., Shamdasani, J., Khodadadi, M.: A novel approach and practical algorithms for ontology integration. In: Proceedings of 17th International Semantic Web Conference (ISWC) (2018).

Tang, K., Kao, H., Chou, J., Chang, E.: Inquire and diagnose: Neural symptom checking ensemble using deep reinforcement learning. In: 3rd Deep Reinforcement Learning Workshop (2016).

Tran, T., Cimiano, P., Rudolph, S., Studer, R.: Ontology-based interpretation of keywords for semantic search. In: Proc. of the 6th Int. Semantic Web Conference and 2nd Asian Semantic Web Conference, ISWC + ASWC. pp. 523-536 (2007).

Vandic, D., Aanen, S., Frasincar, F., Kaymak, U.: Dynamic facet ordering for faceted product search engines. IEEE Transactions on Knowledge and Data Engineering 29(5), 1004-1016 (2017).

Wei, Z., Liu, Q., Peng, B., Tou, H., Chen, T., Huang, X., Wong, K., Dai, X.: Task-oriented dialogue system for automatic diagnosis. In: Proc. of the 56th Annual Meeting of the Association for Computational Linguistics, ACL. pp. 201-207 (2018).

Wessel, M., Acharya, G., Carpenter, J., Yin, M.: OntoVPA–an ontology-based dialogue management system for virtual personal assistants. In: 8th International Workshop on Spoken Dialog Systems, IWSDS. pp. 219-233 (2017).

Yan, Z., Duan, N., Chen, P., Zhou, M., Zhou, J., Li, Z.: Building task-oriented dialogue systems for online shopping. In: Proceedings of the Thirty-First AAAI Conference on Artificial Intelligence (AAAI). pp. 4618-4626 (2017).

Written Opinion of the International Searching Authority for PCT/GB2019/051878, dated Oct. 2, 2019, 5 pages.

Notification of Transmittal of the International Search Report and the Written Opinion of the International Searching Authority, or the Declaration for PCT/GB2019/051878, dated Oct. 2, 2019, 6 pages.

Juric, D., et al., "Reasoning with Textual Queries: A Case of Medical Text", 4 pages.

* cited by examiner

COMPUTER IMPLEMENTED METHOD FOR EXTRACTING AND REASONING WITH MEANING FROM TEXT

FIELD

Embodiments described herein relate to methods and apparatus for extracting meaning from text.

BACKGROUND

Computers are ubiquitous in performing and supporting humans to perform many data analysis tasks. Methods of storing, manipulating and accessing numerical data are well known. However, humans have well developed rules on how to handle numerical data.

However, the situation is not the same for textual data. Text can be used to convey complex meaning and knowledge and this can be done in various different but equivalent ways. However, the techniques for extracting the meaning conveyed in text and reasoning with it are still not well developed as text understanding and reasoning is a highly difficult problem.

Ontologies have been developed to capture and organise human knowledge and Semantic Web standards (e.g., RDF and OWL) is one set of tools for encoding such knowledge in a formal machine understandable way. Ontologies can be used to describe the meaning of textual data and provide the vocabulary that is used by services to communicate and exchange information or by users to access and understand the underlying data.

SNOMED (Systematized Nomencalture of Medicine) is a systematically organised computer processable collection of medical terms providing codes terms, synonyms and definition used in clinical documentation. SNOMED has four primary core components:

Concept Codes—numerical codes that identify clinical terms, primitive or defined, organized in hierarchies Descriptions—textual descriptions of Concept Codes Relationships—relationships between Concept Codes that have a related meaning Reference Sets—used to group Concepts or Descriptions into sets, including reference sets and cross-maps to other classifications and standards Other knowledge bases such as NCI, UMLS, and more have been used extensively in both academic and industrial applications.

However, it is not practical to expect every user to learn the exact schema of a given ontology and input queries or data in the exact desired form. Also, it is not practical to convert every knowledge base into exactly the same format. Thus, there is a need to develop a level of interoperability between the existing methods for storing text based knowledge and also the way in which users will query such stored knowledge.

The developments of some standard is just the first step towards achieving adequate levels of such interoperability. In a vast majority of user inputted queries and stored knowledge, the meaning of a concept in an ontology may still be implicitly encoded in free text, e.g., in its label or in other datatype properties, and not in the form of ontological axioms.

Concepts in SNOMED are defined using codes, e.g., concept 161006, 310497006, etc. For readability reasons hereon instead of using codes, labels will be used that represents the intended real-world meaning of a concept. For example, SNOMED concept 161006 intends to capture the notion of a "Thermal Injury" while concept 310497006 the concept of a "Severe Depression". Hence, instead of "concept 310497006"—"concept SevereDepression" will be used.

Although SNOMED is a large and well-engineered ontology it contains several concepts for which their precise meaning lays "hidden" in their text label and is not reflected with OWL axioms. For example, the concept ThermalInjury in SNOMED has specified in its text label that it is an "Injury due to increased heat". ThermalInjury is also declared to be a subclass of the concept TraumaticAbnormality. The fact that ThermalInjury is a type of Traumatic Abnormality has therefore been formally captured within SNOMED via the subClassOf axiom. However the fact that is an "injury due to increased heat" has not been formally captured since this information is only present within the text label.

Other examples include SevereDepression, which is not defined in terms of SNOMED concepts Depression and Severe, CardiacMuscleThickness, which is not defined in terms of CardiacMuscle and Thick, and many more. This definitional "incompleteness" makes it hard to compare different but equivalent concepts in real-world semi-automated applications. Hence, even if the meaning of text is represented using ontologies, comparing these annotations still posses a lot of challenges.

In addition, an ontology can only contain a finite number of "elementary" concepts (or atomic concepts) which are building blocks for other real-world notions which may or may not be pre-defined in the ontology. Hence, these elementary concepts can be used to build concepts that are not necessarily pre-defined in SNOMED or the like.

For example, concept "recent head injury" can be defined in (at least) the following two ways using SNOMED elementary concepts:

$C_1$:=RecentInjury⊓∃findingSite.HeadStructure
$C_2$:=HeadInjury⊓∃temporalContext.Recently It can be verified using an OWL reasoner such as ELK that it does not follow from the SNOMED ontology that $C_1$ and $C_2$ are equivalent. This is because although in SNOMED HeadInjury is defined in terms of Injury and HeadStructure, RecentInjury is not defined in terms of Injury or Recently. Hence, in order for different services of an application to communicate in an interoperable way they must always pick only one of the two ways to represent the above concept.

Providing effective ways to compare concepts like those presented above is very challenging. It requires exploiting both structured as well as unstructured (textual) information and data to perform such a comparison. For example, in the above two concepts one would require both to analyse the textual content and information that is attached to the concept and explicate their hidden meaning in the form of formal axioms. Afterwards, a logical comparison can be performed.

Embodiments described herein seek to at least partially address some of the problems stated above.

Definitions

In this specification, the term "Simple Concept" means an elementary entity intended to refer to some real-world notion and is interpreted as a set of things. Examples of simple concepts are: Human, Male, TallPerson, and Chairs. Simple concepts are also referred to as "Atomic Concepts" and in OWL jargon, concepts are also called "Classes".

A "Role", "Relation", or "Property" is an entity that denotes relations between objects. Examples of this are hasChild, hasDiagnosis, and isTreatedBy.

The symbol $\pi$ represents logical conjunction. It is called AND for short. It can be used to form the conjunction of two concepts and create a new one. The conjunction of two concepts is interpreted as the intersection of the sets to which the two concepts are interpreted. For example: Professor $\pi$ Male which represents the notion of a male professor. As a whole it is a concept. It is interpreted as the intersection of the sets to which concepts Professor and Male are interpreted.

The symbol $\exists$ (a reversed capital letter E) is defined as the existential operator. It is called EXISTS for short. It can be used with a role and possibly combined also with a concept to form a new concept. For example: $\exists$hasChild represents the set of all things that have some child. Also: $\exists$hasChild.Male represents the set of all things that have a child, where the child is male.

The symbol $\models$ means "entails". It is used to denote that something follows logically (using deductive reasoning) from something else. For example: $\exists$hasChild.Male $\models$ $\exists$hasChild since if someone has a child which is male, then it follows that they necessarily have some child.

The symbol $\sqsubseteq$ is defined as the subclass operator (or the inclusion operator). It denotes a subclass relationship between two concepts. If one concept C is a subclass of another concept D, then the set to which C is interpreted must be a subset of the set to which D is interpreted. It can be used to form axioms. Intuitively it can be read as IF-THEN. For example: Male$\sqsubseteq$Person can be read as "If something is a male then it is also a person".

The symbol $\subseteq$ has the standard set theoretic meaning of a subset relation between sets.

The difference between the symbol $\subseteq$ and $\sqsubseteq$ is that the latter denotes inclusion relation between classes. Classes are abstractions of sets. They don't have a specific meaning but meaning is assigned to them via interpretations. So when Male is written as a class it acts as a placeholder for some set of objects. Hence Male$\sqsubseteq$Person means that every set to which Male is interpreted is a subset of every set that Person is interpreted. This relation is written as:
Male$^J \subseteq$Person$^J$
Where J is called an interpretation and it is a function that maps classes to sets. Hence, Male$^J$ is a specific set of objects.

An "axiom" is a statement or property about our world that must hold true in all interpretations. An axiom describes the intended meaning of the symbols (things). Male$\sqsubseteq$Person is an example of an axiom.

A "knowledge base" or "ontology" is a set of axioms which describe our world. For example, the knowledge base {Male$\sqsubseteq$Person, Father$\sqsubseteq$hasChild.Person} contains two axioms about our world; the first is stating that every male is also a person (the set to which Male is interpreted is a subset of the set to which Person is interpreted) while the latter is stating that every father has a child that is a person (the set to which we interpret Father is a subset to the set of things that have a child that is a Person)" There are several well-known publically available medical ontologies e.g. UMLS, FMA, SNOMED, NCI and more.

A "complex concept" is an expression built using simple concepts and some of the aforementioned operators. The resulting expression is again a concept (an entity denoting some set of things). Professor$\pi$ Male as used above is an example of this. A further example is Person$\pi\exists$hasChild.Male, where Person and $\exists$hasChild.Male are two concepts and Person$\pi\exists$hasChild.Male is their conjunction. This complex concept is interpreted as the intersection of the sets to which Person is interpreted and to which $\exists$hasChild.Male is interpreted. Intuitively this expression intends to denote the set of things that are persons and have a child that is a male.

A knowledge base (KB) (or ontology) can entail things about our world depending on what axioms have been specified in it. The following example is provided to aid the understanding of this idea and the definitions above.

Let $\mathcal{O}$ be the following ontology:
$\mathcal{O} \models$ {Female$\sqsubseteq$Person, HappyFather$\sqsubseteq\exists$hasChild.Female, $\exists$hasChild.Person$\sqsubseteq$Parent}.

Then from this, it can be deduced that $\mathcal{O} + \models$ HappyFather $\sqsubseteq\exists$hasChild.Person This inference can be made because given the ontology that every female is a person and a happy father must have at least one child that is a female, it follows using deductive reasoning every happy father must have a child that is a person.

Similarly, it can also be inferred that $\mathcal{O} \models$ HappyFather $\sqsubseteq$Parent.

An "IRI" is an Internationalized Resource Identifier which is a string of characters that identifies a resource. It is defined as a new internet standard to extend upon the existing URI uniform resource identifier, the commonly used URL is a type of URI relating to location.

A "reasoning algorithm" (or reasoning system) is a mechanical procedure (software program) which given an ontology (aka knowledge base) can be used to check the entailment of axioms with respect to the knowledge specified in the ontology. In the previous example, $\mathcal{O}$ can be loaded to some reasoning algorithm and then check if HappyFather$\sqsubseteq$Parent is entailed by $\mathcal{O}$. Reasoning algorithms are internally based on a set of "inference rules" which they apply iteratively on the axioms of the ontology and the user query in order to determine whether the axiom is entailed or not. Depending on the set of inferences rules that a reasoning systems implements it may or may not be able to discover the entailment of an axiom even in cases that this is actually entailed. A reasoning system may implement a "weak" set of inferences rules in order to be able to handle large ontologies in a scalable way whereas other reasoning systems may favour to answer correctly all cases and hence implement a more expressive set of inference rules. The former usually implement only deterministic inference rules whereas the latter a non-deterministic one.

A "triple-store" is a particular type of reasoning system that supports entailment of ontologies expressed in the RDF(S) standard. Such reasoning systems are generally efficient and scalable, however, if the ontology is expressed in more expressive standards like OWL they will not be able to identify all entailments. For example, standard triple-stores will not be able to answer positive on the query HappyFather$\sqsubseteq$Parent over the ontology $\mathcal{O}$ in the previous example.

DETAILED DESCRIPTION

Figure 1A:
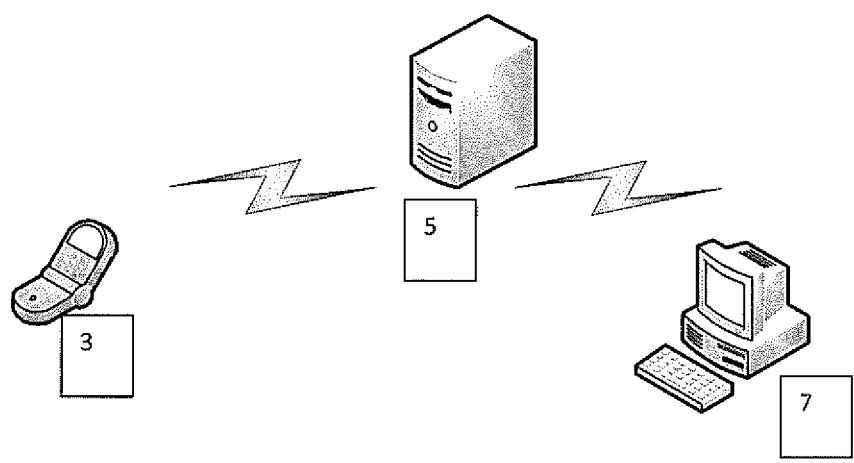
FIG. 1A is a schematic of a system in accordance with an embodiment.

In an embodiment, a text processing method is provided for improving the accuracy of a response to a query directed to a system comprising concepts and relations defined by a knowledge base, wherein the method comprises:

(1.i) producing a dependency tree from the query, wherein the dependency tree has at least one branch containing nodes and at least one connection between those nodes, wherein each node has a node label which corresponds to a term within the query, and wherein each connection has a label which corresponds to the linguistic relationship between terms within the query;

(1.ii) from the dependency tree, generating a query concept using concepts and relations defined by the knowledge base;

(1.iii) checking if the query concept has a subsumption relationship with a candidate concept retrieved from the system, and if no subsumption relationship is initially identified, optimising the dependency tree by changing the nodes, followed by repeating steps (1.ii) and (1.iii); and wherein the query concept and the candidate concept comprise at least one atomic concept.

The above method is a computer implemented method that allows a computer to extract meaning from text and to be able to perform reasoning with such text, without requiring further human intervention. This allows a computer to efficiently and accurately identify the subject matter of a query such that subject matter that relates to the query can be easily retrieved. Processing a query input in this way potentially allows a computer to return a response to a query using less computing resources since the above method allows a more accurate response to the query to be initially provided or in some embodiments allows more generic, but relevant information relating to the query to be returned as opposed to failing to provide a response.

The above method compares (with reference to subsumption) concepts by exploiting "meaning" that is encoded in their text labels and axioms that are stated for the used entities in some background Knowledge Base. The computer-implemented method extracts concept definitions from small text phrases attached to concepts, e.g. "recent head injury". The method first uses Natural Language Processing (NLP) techniques to discover the dependencies between the words in such phrases and then picks a proper relation between them to form an OWL concept expression. The method does not assume full sentences that necessarily contain verbs or any pre-existing set of training examples as is used in existing techniques. The method is then combined with logic-based reasoning techniques to provide a novel concept comparison (w.r.t. subsumption) algorithm that uses both logical and textual information.

The method of the above embodiment has real-world industrial strength uses cases. The method is used in digital health services such as AI-based chatbot and virtual doctor consultation. Clinical history and findings for a patient can be stored using concepts from medical ontologies.

In an embodiment, the Knowledge Base is loaded into some in-memory triple-store which uses its own custom data structures and indexes to store the triples (classes/properties). The data from the triple-store are retrieved using SPARQL and keyword based queries the latter of which are performed on the labels of the entities that exist in the KB. The labels of the entities can be indexed using a search and analytics engine such as elasticSearch when loading the data to the triple-store. Both SPARQL and elasticSearch can use end-points/connectors by a GraphDB triple-store.

In an embodiment, complex concepts have a tree-like form and can be stored using a custom tree-like data mode where every node of the tree contains an IRI and the corresponding (preferred) label of the IRI and edges between nodes also contain the IRI of some property (relation) and its (preferred) label. When checking for subsumption between the IRIs attached to the elements of the two trees (two complex concepts for comparison hence 2 trees), the trees are traversed.

In the above, the query concept and/or candidate concept is a complex concept comprising more than one atomic concept. Also, the changing of nodes comprises the merging and/or deletion of nodes.

In an embodiment, the optimisation of the dependency tree uses the linguistic relationship between terms to decide whether to change the nodes. For example, if the linguistic relationship between some terms is that the terms form part of a multi-word expression, the nodes representing those terms are merged. In a further example, if the linguistic relationship between some terms is that one of the terms is a preposition or case, then the node for that term is deleted.

In a further example, the optimisation of nodes comprises the following steps:

a. Select a primary node;
b. For each child of the primary node:
  i. Select that child node as the secondary node
  ii. Recursively perform this optimisation process on the secondary node so that the optimisation process begins at the end of a branch of the dependency tree;
  iii. If the linguistic relationship is that the terms of the primary and secondary node form part of a multi-word expression, then the nodes for those terms are merged;
  iv. If the linguistic relationship between some terms is that one of the terms is a preposition or case, then the node for that term is deleted;
  v. If the secondary node is merged or deleted, attaching the children of the secondary node to the primary node.

The optimisation of nodes may further comprise selecting a sequence of nodes, joining together the labels of those nodes trying different combinations to form a chunked label, comparing the chunked label to concepts defined by a knowledge base, and if a matching concept is found, merging the nodes into a single chunked node having the chunked label as the label for the chunked node.

In a further embodiment, in the generation of the query concept, the linguistic relationship between terms determines how to select concepts and relations defined by the knowledge base for use in the query concept.

For example, if the linguistic relationship between some terms is that one of the terms is a nominal or modifier, the following steps may be performed:
a. From the terms, selecting concepts based on the labels of the nodes for the terms;
b. Identifying semantic types of the concepts;
c. From the semantic types, selecting the most likely relation between those types;
d. Appending the relation and concepts to the query concept.

If the linguistic relationship between some terms is that two or more non-verb terms are linked by a verb term, the following steps may be performed:
a. Selecting concepts based on the non-verb node labels;
b. Selecting a relation based on the verb node label;
c. Appending the relation and concepts to the query concept.

The generation of the query concept may comprise the following steps:
a. Select a node as a primary node;
b. Select a first concept based on the label of the primary node;
c. Obtain the semantic type of the first concept;
d. Initially define the query concept as the first concept;
e. For each child node of the primary node:
  i. Select that child node as the secondary node;
  ii. If the linguistic relationship is such that the label of the secondary node is a nominal or modifier:
    1. Select a second concept based on the label of the secondary node;
    2. Obtain the semantic type of the second concept;
    3. Choose the most likely relation based on the semantic types of the first and second concept;
    4. Append the relation and the second concept to query concept;
    5. Recursively perform this query concept generation process on the secondary node, selecting the secondary node as the primary node in step (i) above, such that the concepts and relations subsequently identified are appended to query concept;
  iii. If the linguistic relationship is that the label of the secondary node is a verb:
    1. Select a relation based on the label of the secondary node;
    2. Select a second concept based on the label of the first child of the secondary node;
    3. Append the relation and the second concept to the query concept;
    4. Recursively perform this query concept generation process on the first child of the secondary node, selecting the first child of the secondary node as the primary node in step (i), such that the concepts and relations subsequently identified are appended to the query concept.
f. Return the query concept.

In an embodiment, checking for a subsumption relationship may comprise:
a. Determining if the first concept of the query concept is subsumed by the first concept of the candidate concept;
b. Determining whether for each relation in the query concept, there is a relation in the candidate concept that subsumes it, and for each concept in the query concept there is a concept in the candidate concept that subsumes it.

Checking for a subsumption relationship may further comprise:
a. choosing an axiom from the knowledge base with a structure: concept-relation-concept, wherein the first concept of the axiom corresponds to a concept from the query concept;
b. using the axiom in place of the concept from the query concept when checking the subsumption relationship.

In a further embodiment wherein step (1.iii) further comprises additional comparisons between the query concept and the candidate concept and the results of these comparisons are used to decide whether to further optimise the dependency tree. The additional comparisons may comprise calculating a score for the similarity between a label of the query concept and a label of the candidate concept. Also, if the score for the similarity is below a predetermined threshold, the step of optimising the dependency tree is not performed and it is determined that there is no subsumption relationship between the query concept and the candidate concept. The score may be calculated using Levenshtein distance, Needle-Wunch, or Smith-Waterman algorithms.

In an embodiment, the score for the similarity is calculated between the label of an atomic concept of the query concept and the label of each atomic concept of the candidate concept, and wherein the optimisation is only not performed if all of these scores for the similarity fall below the predetermined threshold.

In a further embodiment, the method returns a confidence value that is reduced each time the optimisation is performed.

In an embodiment, the further comparisons may comprise:
a. Determining whether for each relation in the query concept, there is a relation in the candidate concept that subsumes it, and for each concept in the query concept there is a concept in the candidate concept that subsumes it;
b. if this test returns true, performing further optimisations on the candidate concept;
c. if this test returns false, performing further optimisations initially on the query concept;

Also, after the further optimisation has been performed for either the query concept or the candidate concept, it may be again checked whether there is a subsumption relationship; if no subsumption relationship is identified then further optimisation is performed on the other concept.

In a further embodiment, a text processing method is provided for more accurately converting a query into concepts and relations defined by a knowledge base, wherein the methods comprises:
a. producing a dependency tree from the query, wherein the dependency tree has nodes, wherein each node has a node label which corresponds to a term within the query, and the dependency tree has connections between the nodes, wherein each connection has a label which corresponds to the linguistic relationship between terms within the query;
b. from the dependency tree, generating a query concept using concepts and relations defined by the knowledge base;
c. optimising the dependency tree by merging nodes and/or deleting nodes followed by repeating step b.

In the above embodiments, the optimisation of nodes further comprises selecting a series of nodes, appending together the labels of those nodes to form a chunked label, comparing the chunked label to concepts defined by a knowledge base, and if a matching concept is found, merging the nodes into a single chunked node having the chunked label as the label for the chunked node. FIG. 1A is a schematic of a system in accordance with an embodiment. A user 1 uses their mobile telephone 3 to contact a web based medical service. The web based medical service comprises a diagnostic engine 5. A diagnostic engine (which will not be described in detail here) generates a list of possible causes for an inputted system or list of symptoms. Possible types of diagnostic engines that can be used are based on probabilistic graphical models, such as Bayesian networks and possible causes for the symptoms can be generated using inference techniques. The diagnostic engine will define these conditions, symptoms, diseases etc using concepts which are defined within a knowledge base.

Alternatively, the diagnostic engine may instead be a medical records system storing the recorded conditions for the user inputting the query. One can use the methods of the invention to improve quality of the comparison of input text to the medical records system to identify which condition the user intends in their message.

For example, a user may input the text "My leg is in great pain" and the chatbot engine may output the complex concept Pain$\pi\exists$findingSite.Leg. The diagnostic engine 5 may contain a node annotated with concept "FootPain". Using the invention we can compare the two concepts and identify that the respective node in the diagnostic engine needs to be activated in order to push to the user questions regarding conditions related to FootPain. Using the method the invention, a computer can better understand a user query in terms of the semantic concepts used.

Also, it is possible to compare medical concepts that are produced, consumed, and exchanged by various services. For example, medical concepts created by analysing user input text in a chatbot can be compared to past patient diagnosis from their profile, which may be stored at medical centre 7 as well as with medical conditions in the diagnostic engine 5. The text data from the medical centre can be used to properly instantiate nodes in a diagnostic engine and reduce the number of questions being asked to the user of the chatbot.

Figure 1B:
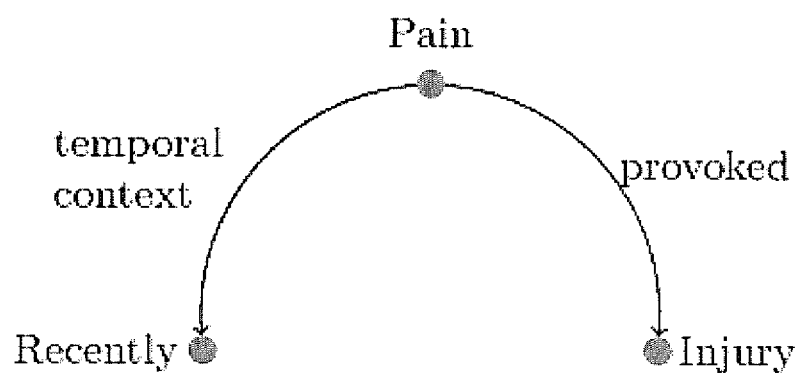
FIG. 1B is a graph depicting the desired decomposition of the medical phrase "recent pain provoked by injury" into linked tokens.
Figure 1C:
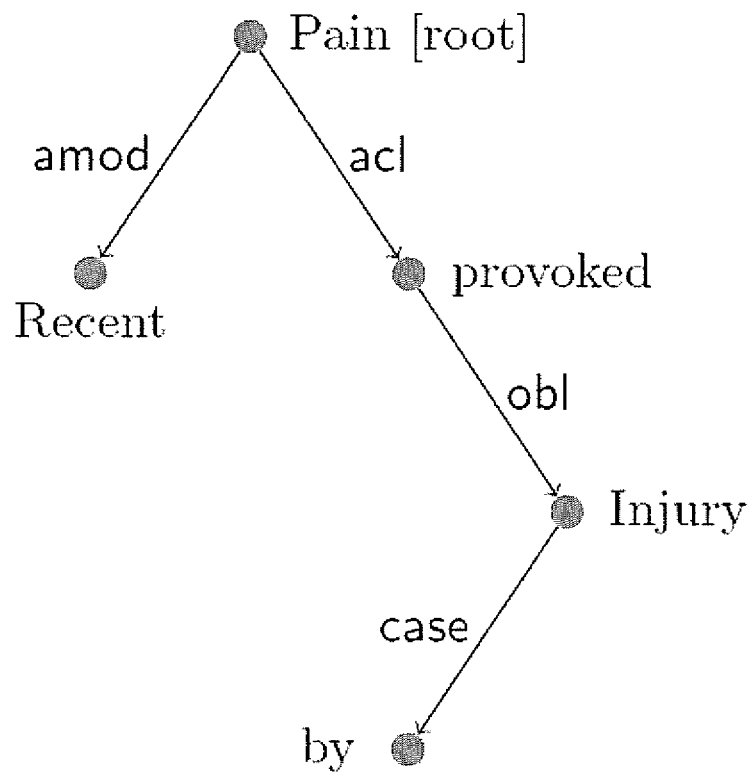
FIG. 1C is a diagram depicting a dependency tree produced by a NLP process on the medical phrase "recent pain provided by injury".
Figure 1D:
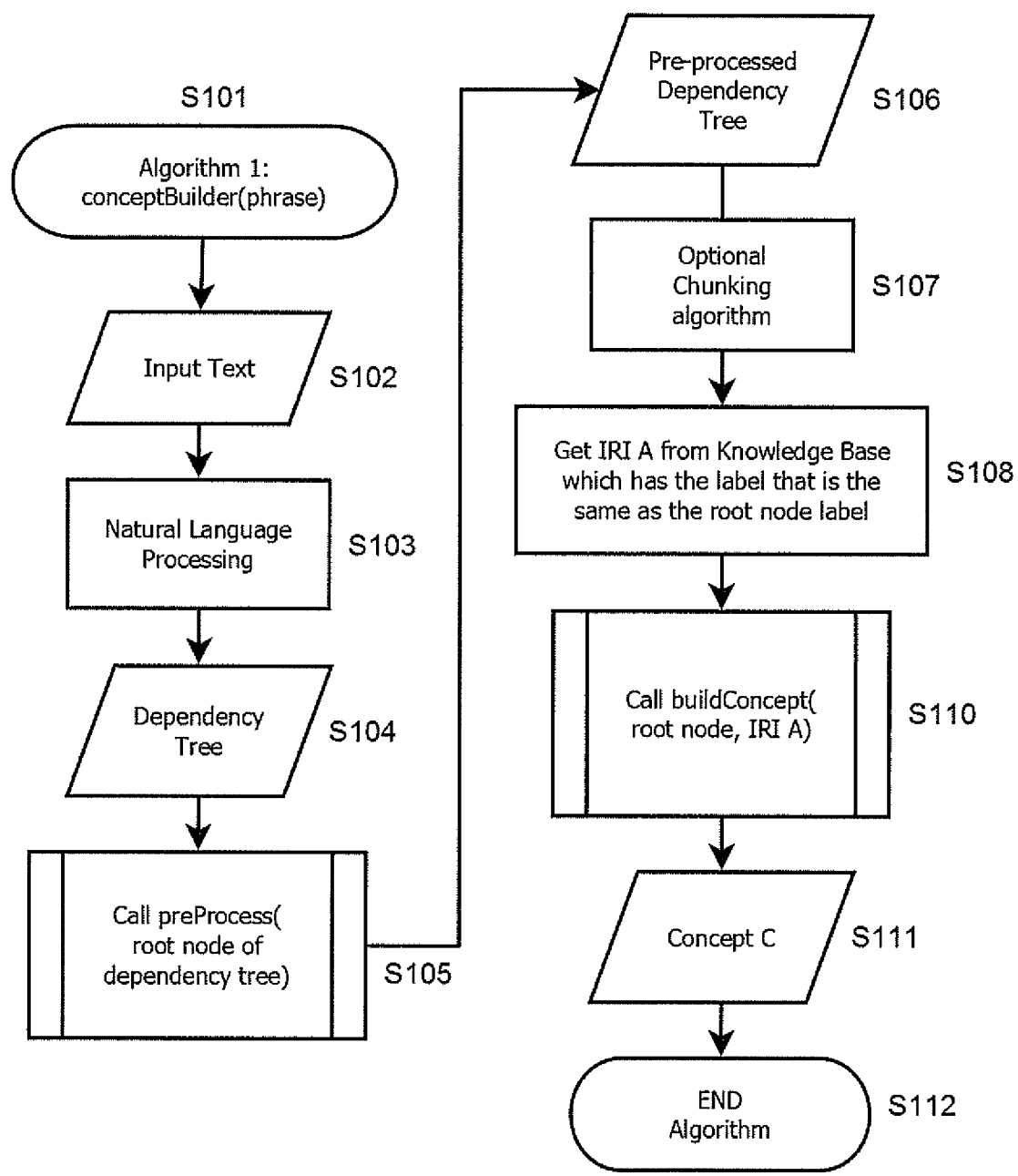
FIG. 1D is a flowchart depicting an overview of the steps of Algorithm 1.
Figure 1E:
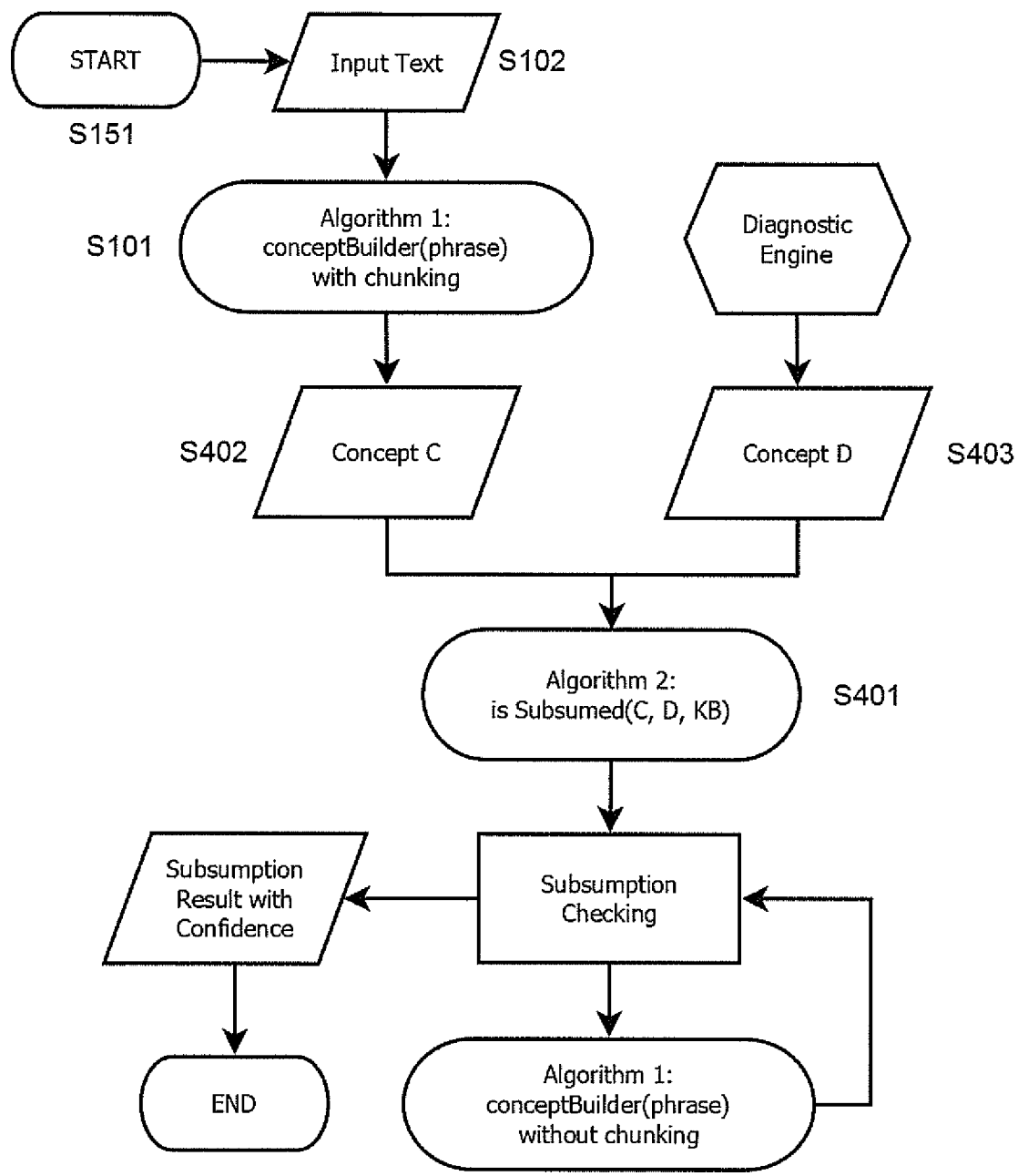
FIG. 1E is a flowchart depicting an overview of the steps of a process according to a first embodiment of the invention.

The overall method of the invention is depicted in FIG. 1E. The individual steps of this method are described in detail below. Input text is obtained from a data source such as user input or some medical database. Algorithm 1 is then executed on the input text including the optional chunking function.

Algorithm 1 uses NLP techniques to generate a dependency tree with nodes representing the individual words from the input text. Algorithm 1 then optimises the dependency tree. This is performed based on the linguistic relations between the nodes to merge and delete nodes. It also uses the chunking function to compare groups of words to concepts in the knowledge base, in order to merge nodes. The end result of Algorithm 1 is a (complex) concept defined in terms of concepts.

Next the concepts are then compared using Algorithm 2 to concepts defined in the diagnostic engine using subsumption. If the concept C (derived from Algorithm 1) is not subsumed by concept D (obtained from the diagnostic engine), then Algorithm 2 must consider whether to run Algorithm 1 on concept C and/or concept D without the optional chunking. It makes this decision by comparing the labels of the concepts within C and D. If the string similarity is high enough that it suggests relation between concepts C and D then Algorithm 1 can be executed.

After Algorithm 1 has been executed and concept C or D has been further broken down, the concepts are again checked for subsumption. If the reasoner indicates that there is a subsumption relationship (i.e. Algorithm 2 returns TRUE for the selected concept D) then concept D from the diagnostic engine is selected as one of the possible concepts which corresponds to condition described in the input text.

A system using these algorithms can use this to help identify the disease which the user means in their message with improved accuracy, a reduced number of questions, and a faster response such as a result of the greater specificity of the query.

Algorithm 1—Extracting Concept Definitions from Text

In the current section, invention method for building concept definitions from medical concepts described in text will be explained. Such concepts (which will be called medical phrases) follow certain patterns and in many occasions contain a large number of tokens. Some representative examples:

Diseases: "acute duodenal ulcer with perforation"; "acute infantile liver failure due to synthesis defect of mitochondrial deoxyribonucleic acid encoded protein".

Clinical findings: "granuloma surgical wound"; "central sleep apnea caused by high altitude".

Anatomical structures: "entire arbor vitae of cerebellum"; "vascular transformation of lymph node sinuses".

Procedures: "radionuclide imaging of adrenal gland using iodocholesterol"; "care of subject following general anesthesia".

In order to construct concept definitions for them the first important step is to decompose these phrases into tokens and discover relationships between them. FIG. 1B depicts the desired decomposition of the medical phrase "Recent pain provoked by injury". In an embodiment, the method decomposes the phrase into the depicted graph in which nodes correspond to words from the phrase (wherein the nodes are ultimately linked to knowledge base (KB) concepts) while the edges represent linguistic relations between the words (wherein the relations would ultimately be mapped to KB relations). This kind of decomposition is an attempt to explicate the semantics that are hidden in the textual description and can then be used to build a concept which can be used in reasoning and thus for comparison of meaning.

A natural linguistic approach of dependency parsing for the input transformation algorithm is used. A dependency parser takes as an input a phrase, brakes it into tokens and returns a dependency tree of the type shown in FIG. 1C. An important part of the tree is its root (also called the base token) that determines the context of the phrase. The rest of the tokens are recursively appended to it and represent the modifiers of the base or other joining tokens of it. Edges in the tree are annotated with the linguistic information that relates the tokens and which are used to assign semantics to the phrase.

A shown in FIG. 1C, in an embodiment, the function takes as input a phrase and returns a labelled tree, where each node (node) is labelled with its corresponding word found in text (denoted by node.l) and each edge $<node_1,node_2>$ (i.e. the connection between those nodes) with the linguistic relation that related the words (denoted by $<node_1,node_2>.l$). There are several types of linguistic relations, however, after experimenting with medical phrases only a subset of them are relevant. Definitions of these dependencies can be found in Universal Stanford Dependencies: A cross-linguistic typology (de Marneffe et al. 2014) with a revised list available at www.universaldependencies.org/u/dep. These relations are:

MWE: this class denotes that the adjacent nodes in the tree represent a "multi-word expression". For example, in the phrase "Heart Attack", "Attack" and "Heart" would be adjacent tree nodes linked with the relation "compound".

FunctionWords: class of linguistic relations that denotes that in adjacent nodes in the tree the child is a preposition ("prep") or "case" (e.g. a word such as "by").

NominalsAndModifierWords: that in two adjacent nodes in the tree the child is a modifier of the parent node; e.g. in phrase "severe pain", "pain" would be root node and "severe" its direct child that modifies it. Relations in this class include "nmod", "npadvmod", "advmod", "obl", "pobj", "dobj", and "nsubj".

Clauses: class of linguistic relations that denote that in a path of three nodes the middle one is a verb; e.g. in the phrase "Pain provoked by injury", the three nodes would be "Pain", "provoked", and "injury", and the first two nodes would be connected with their edge annotated with "acl". The term "by" being a preposition would be ignored.

The method of converting a phrase, e.g. "recent pain provoked by injury", to the dependency tree shown in FIG. 1C will be referred to as a function termed dependencyParser. As can be seen, this dependency tree is not in the same form as that shown in FIG. 1B, the desired output.

In an embodiment, a method for extracting a concept definition from a medical phrase is given in Algorithm 1 and depicted in FIG. 1D-FIG. 3C. The algorithm accepts an input phrase as input S102 and then calls an NLP dependency parser to tokenize the phrase S103 and build its dependency tree S104 as explained using the dependencyParser function of FIG. 1C. It is to be understood that this dependency parsing is known in the art and that publically available parsers can be readily used. An example of a preferred NLP dependency parser to be used in a method in accordance with an embodiment is available at https://emorynlp.github.io/nlp4j/.

The algorithm then calls the function PreProcess S105 which merges pairs of nodes that are related with linguistic relation "compound" (and which should be treated as one word) as well as skipping function fords like prepositions i.e. nodes that are linked to another node with relation "prep" or "case" are deleted.

PreProcess Function

Figure 2A:
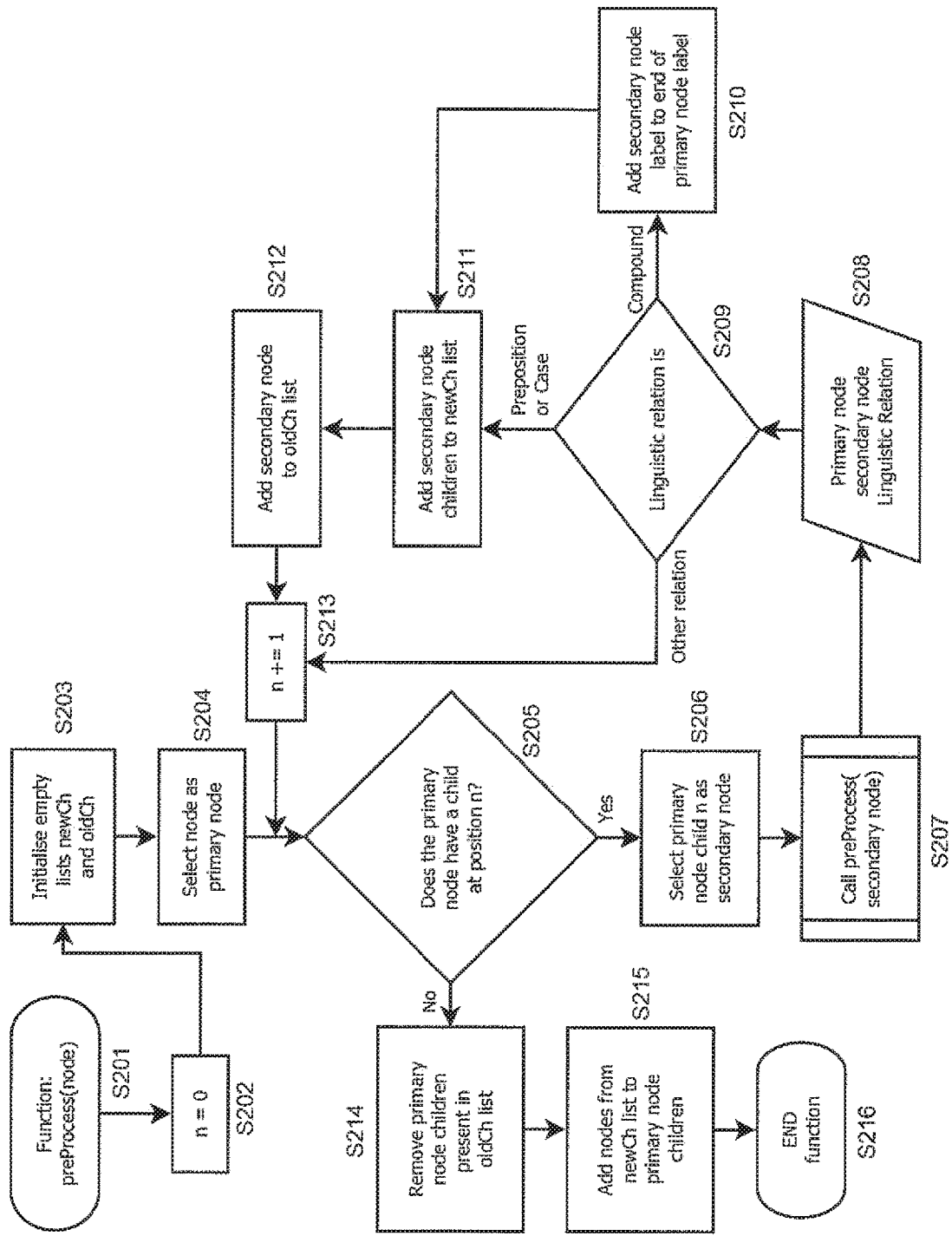
FIG. 2A is a flowchart depicting a first embodiment of a first processing function which forms part of Algorithm 1.
Figure 2:
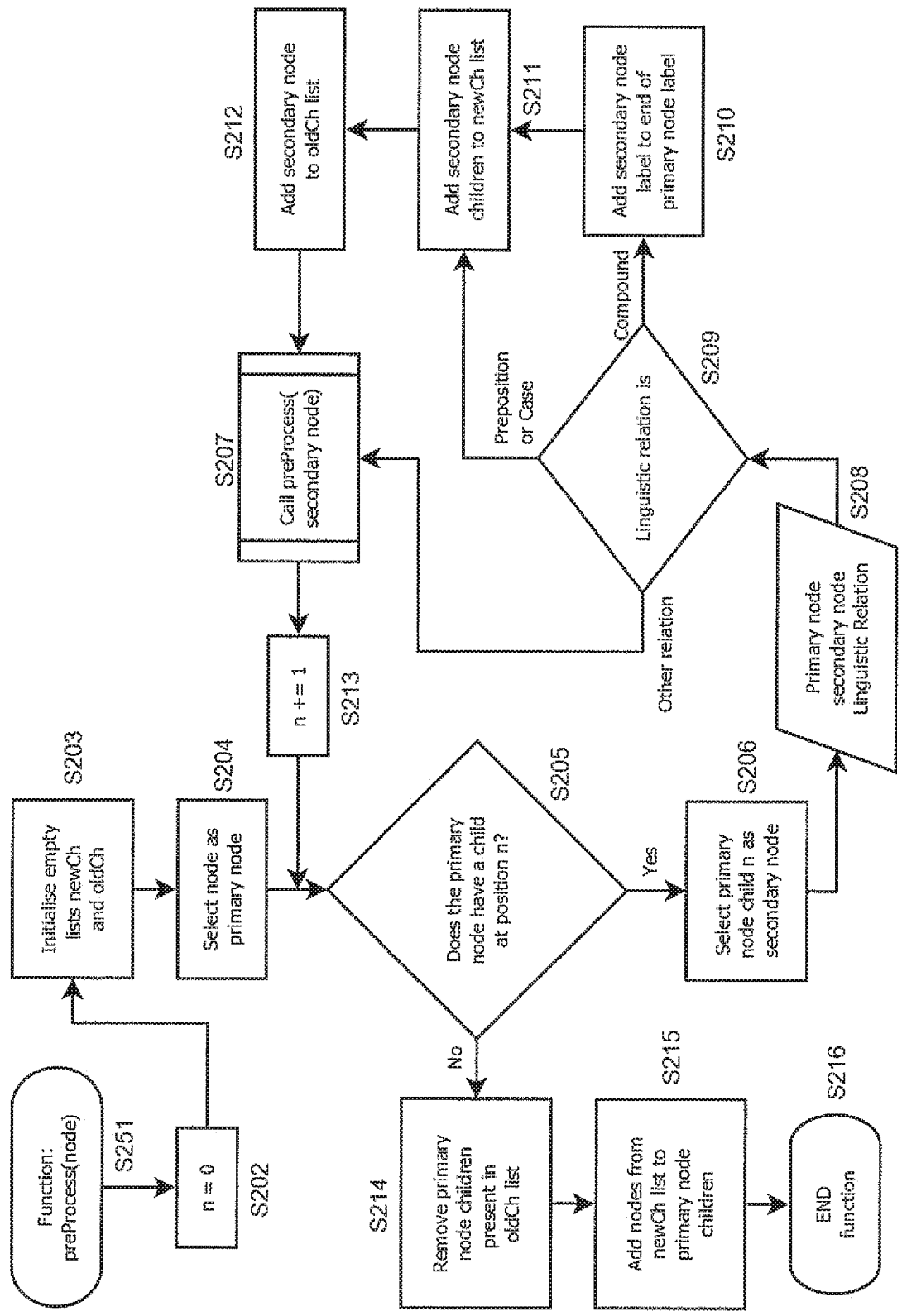
FIG. 2B is a flowchart depicting a second embodiment of a first processing function which forms part of Algorithm 1.

The PreProcess function of S105 is depicted in greater detail in FIG. 2A and FIG. 2B. There are two versions of the function, both versions operate in a depth-first mode. i.e., they always fully process the sub-tree of one child before moving to the next child. The difference on the two algorithms is the order in which they process parent versus child nodes. FIG. 2A is a post-fix order (i.e., one where the parent is always processed after all children; and since children are also processed after their children, it follows that every node is processed after all its descendant nodes have been processed). FIG. 2B is a pre-fix order where a parent is always processed before children.

Looking first at FIG. 2A, since PreProcess is called initially on the root node S201, it begins there. PreProcess initialises a variable n=0 S202 and two empty lists: newCh and OldCh S203. The selected node (initially root) is defined as the primary node S204. The function first checks if the primary node has any children at position n S205. If this is true, then child n of the primary node is selected as a secondary node S206. PreProcess then recursively calls itself on the secondary node S207. This has the effect of stepping down the tree to deepest child node on the first branch as described in the previous paragraph. When the function reaches the deepest child node, the check at S205 will return false, as there are no further children on the branch, and proceed to step S214. The lists recited in steps S214 and S215 are initially empty and so no operations are performed in the first instance. The function is terminated for that child node and thus returns to the parent node above it, with the function for that parent node proceeding to step S208.

The function evaluates the linguistic relation S208 between the primary node and the secondary node S209. If the relation is a compound (i.e. that the primary and secondary node labels represent a multi-word expression) then the label of the secondary node is added to the end of the primary node label S210. In this way, if the primary node label was "Heart", the secondary node label was "Attack", and the dependency parser recognised that there was a "compound" linguistic relation between them then the primary node label would be changed to "Heart Attack".

The children of the secondary node are added to the newCh list S211 and the secondary node itself is added to the oldCh list S212. Following this, n is incremented by 1 S213 and function loops back to determining if there is a child S205. In modern programming languages it is possible to make use of abstractions such as "for" loops which automatically perform the operation of selecting each item in a list or array of items without it being necessary to manually increment an index. This is shown in the pseudo code below where for loops are used.

If the linguistic relation is "prep" or "case", the function does not change the label of the secondary node and instead moves on straight to step S211.

If linguistic relation is any other relation, the function moves to S213.

Once the last child is reach for a given node, decision S205 will return false and the function will go to step S214. Children which were placed in the oldCh list are deleted S214. This removes redundant secondary nodes where the linguistic relations were "compound", "prep", or "case". The children of those secondary nodes, which were added to the newCh list are then added to the children of the primary node S215. Following the "Heart Attack" example above, the function will then delete the redundant "Attack" node and then attach any subsequent nodes which are children of the "Attack" node to the new "Heart Attack" node.

FIG. 2B depicts an alternative embodiment of the PreProcess function where a depth-first pre-fix method is used instead. The two embodiments are largely identical except that step S207 where the function recursively calls itself on the secondary node is performed shortly before the function loops, i.e. before S213, rather than near the beginning of the loop.

In cases where there are no multi-word expressions of more than 2 words, the two embodiments are equivalent. So in the case of just "Heart", "Attack" there would be no difference. However, in the case where there are MWEs of 3 words the embodiment of FIG. 2A directly considers the linguistic relation of a newly created node created from the first and second node of an MWE with the third word of an MWE.

For example, consider the case of the disease Amyotrophic Lateral Sclerosis, which would be initially represented as "Amyotrophic" "Lateral" "Sclerosis" and is a multi-word expression. In the embodiment of FIG. 2B "Amyotrophic" and "Lateral" would be merged to create the node "Amyotrophic Lateral" but since the function then finishes processing the current node (which is now "Amyotrophic Lateral") and moves to the descendant node (which is "Sclerosis") without considering the compound linguistic relationship between "Lateral" and "Sclerosis", and so it will not merge any more of them to the current node, i.e., it will not combine "Amyotrophic Lateral" with "Sclerosis" as it should. The final result will be two nodes, namely "Amyotrophic Lateral" and "Sclerosis" linked with linguistic relation compound but they will never be merged.

In the case of the embodiment of FIG. 1A, the post-fix order means that children will be processed before the current node. Hence, before processing node "Amyotrophic" its children will be processed merging "Lateral" with "Sclerosis" and creating "Lateral Sclerosis". When the function works back up the tree to the node for "Amyotrophic" it will consider the linguistic relation between "Amyotrophic" and "Lateral Sclerosis" and correctly merge these nodes to create the node "Amyotrophic Lateral Sclerosis".

Thus, the embodiment of FIG. 2A can handle MWEs of 3 or more. However, both the embodiments of FIGS. 2A and 2B cope the same with MWEs of at most two words.

Chunking Function

Once the pre-processing of FIG. 2A or 2B is complete and a Pre-processed dependency tree is produced in S106, an optional chunking function S107 can be run on the concepts represented by the nodes in the tree. In a dependency tree of n nodes, the tree will first select all n nodes and concatenate the labels of those nodes to form a string. The function then searches the KB for a concept with a label that matches the concatenated string. If the search identifies a concept that matches the string, then all of the nodes will be merged to form a single concept.

For example, considering a tree with Foot->pain->swelling and, in this example, it will be assumed that the first pre-processing step will not merge any nodes. However, then the nodes would be merged to produce FootPainSwelling. The KB would be then searched using the string FootPainSwelling. If the KB contains the concept FootPainSwelling, then the 3 nodes would be merged into a single node with label FootPainSwelling. This action of grouping nodes together is known as "chunking" since the nodes are being sorted into chunks.

However, if this search is not successful, then the function considers sets of n−1 nodes and searches the KB with the n possible permutations of the n−1 sets. So if the KB did not contain a concept for FootPainSwelling, it would then search the KB for FootPain, FootSwelling, and PainSwelling. If the KB contained, for example, Footpain, then the corresponding nodes would be merged, resulting in "Swelling" and "FootPain". If the function identifies multiple possibilities for valid chunks which could be produced, then it will either select the most probable chunk or if the probability of the most probable chunk is too unlikely, then the function assumes that no chunk is valid for that selection of n−1 nodes.

If, again, a matching concept in the KB is not found, then the function would search the KB for combinations of n−2 nodes. However, these searches will only occur provided there are at least two nodes in the considered chunk. This means that the chunking function will not proceed to search the KB for individual words. So if the search found nothing for the n−1 search described above, on FootPainSwelling, it would not proceed to consider each of "Foot", "Pain", and "Swelling" individually at this stage.

Typically the chunking function is used when Algorithm 1 is first run to generate the initial concept from the input text. However, when Algorithm 1 is run again, i.e. when it is called by Algorithm 2, the chunking function is typically not used. The reason for this is because if Algorithm 1 is being called by Algorithm 2, then it is desirable to attempt to break down the input concept into smaller pieces e.g. individual words, to help identify concepts therein. Nonetheless, it may be advantageous not to use the chunking function when Algorithm 1 is first run and it may be advantageous to use the chunking function when Algorithm 1 is called by Algorithm 2.

BuildConcept Function

Once the pre-processing of FIG. 2A or 2B is complete and a Pre-processed dependency tree is produced in S106, and this tree may have been parsed by the chunking algorithm, algorithm 1 calls the function getIRI in step S108 (line 5 of algorithm 1). getIRI performs an "exact-label" search over a KB in order to obtain a suggested IRI for the given label of a tree node.

For this purpose, in an embodiment, the labels of the concepts in the KB have been indexed using ElasticSearch. ElasticSearch is a known search engine, although other search engines could be used. When starting at the root the only information available is its label. The IRI for the root is picked simply by using this method and selecting the first IRI that is returned by ElasticSearch S108. Since the medical domain is quite specific, ambiguous cases are very rare and the first IRI corresponds in the vast majority of cases, to the intended meaning of the word.

Nevertheless, as the method proceeds to subordinate nodes in the tree (see for example FIG. 1C), the information that has been determined for parent nodes can be exploited to make more confident choices of IRIs as well as to assign a relation between adjacent tree nodes. For example, if a node in the tree has been assigned an IRI that corresponds to a disease then the child node cannot be assigned an IRI that corresponds to a procedure. Optionally, since one knows what the possible types of IRI for the child node are permitted, when getIRI later searches for a matching IRI for that child node, the algorithm can avoid searching for concepts that do not match those possible types. This reduces the search space and can make a query faster. Algorithm 1 calls function BuildConcept which traverses the dependency tree in a depth-first manner trying to assign IRIs to the nodes in the tree and relations between adjacent nodes (except for nodes that contain verbs; see next). Since the structure returned by dependency parsing is a tree, the algorithm essentially generates $\varepsilon\mathcal{L}$ concepts of the form $A\pi\exists R_1.D_1\pi\ldots\pi\exists R_m.D_m$ where each $D_i$ can again be of the same form.

Figure 3A:
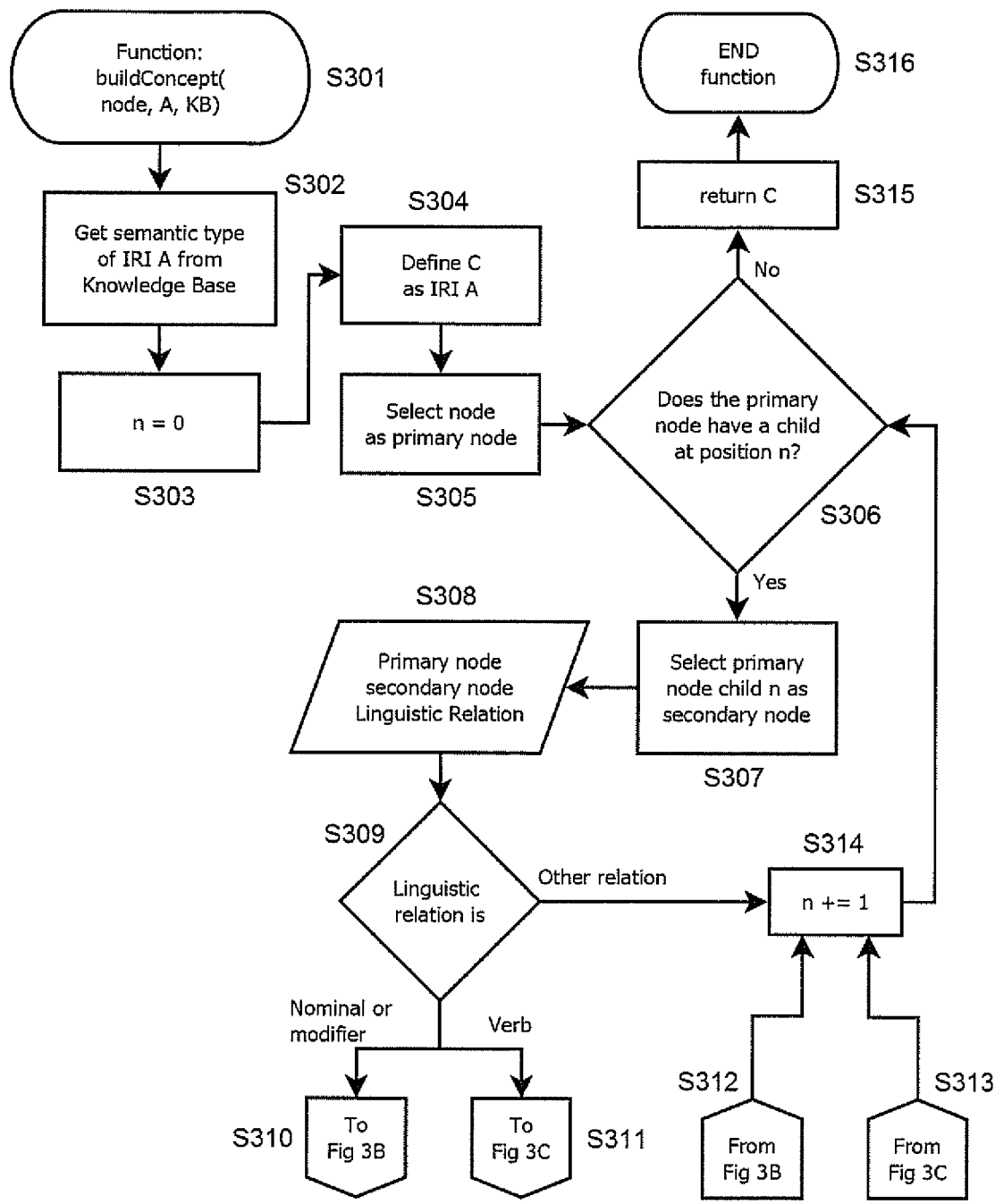
FIG. 3A is a flowchart depicting the first part of an embodiment of a second processing function which forms part of Algorithm 1.
Figure 3B:
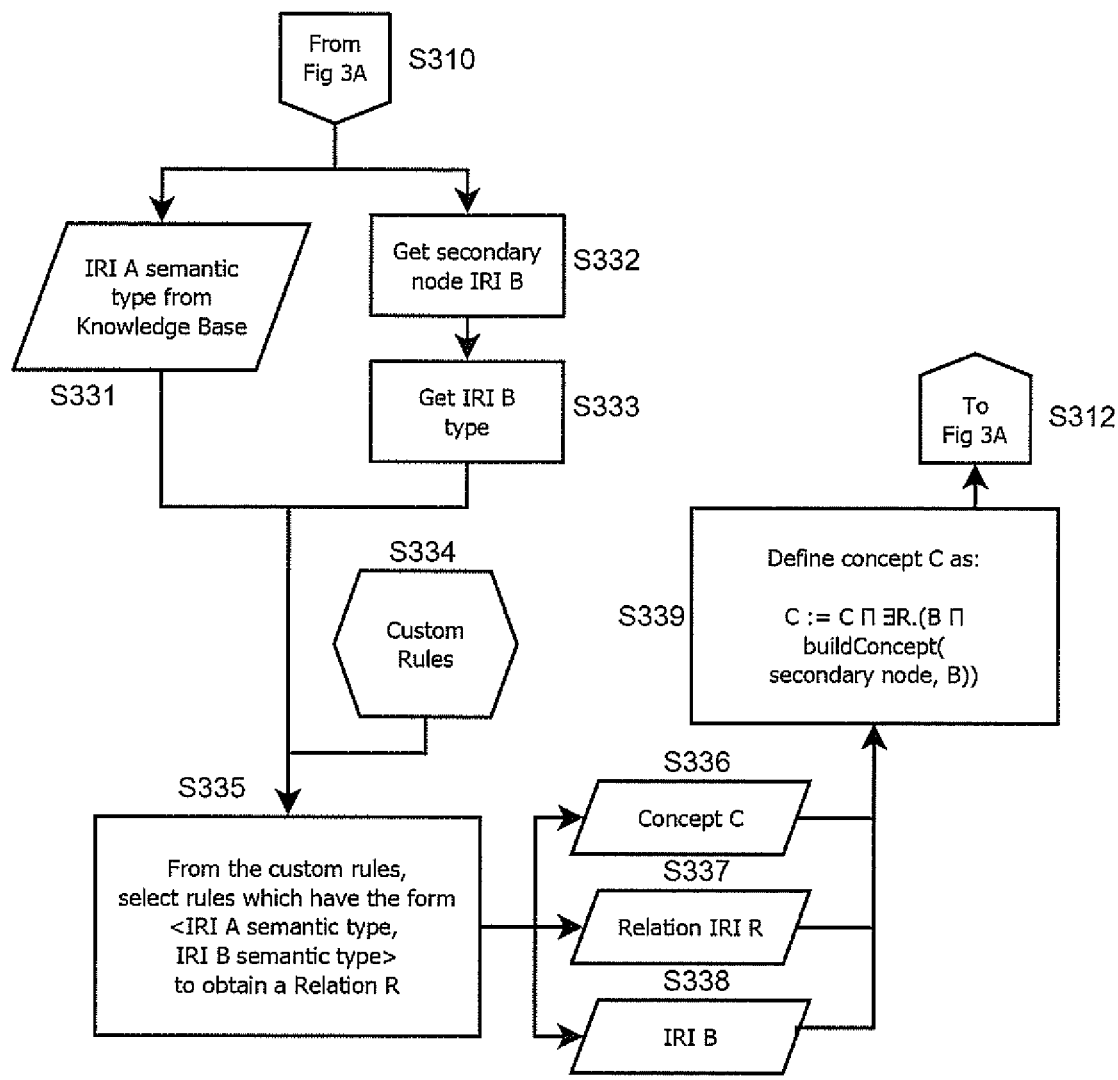
FIG. 3B is a flowchart depicting the second part of an embodiment of a second processing function which forms part of Algorithm 1.
Figure 3C:
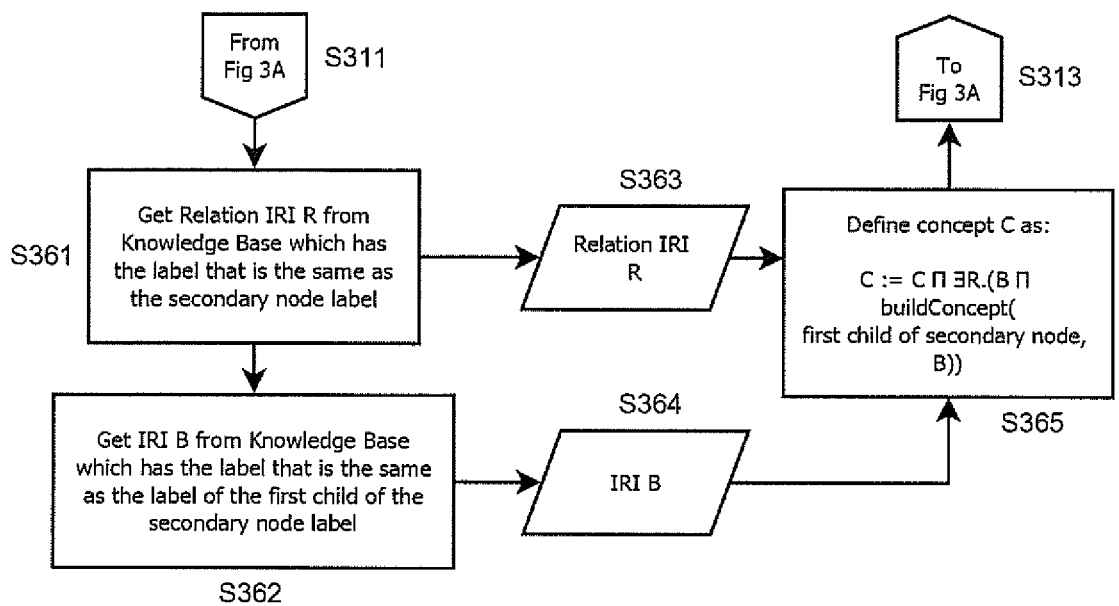
FIG. 3C is a flowchart depicting the third part of an embodiment of a second processing function which forms part of Algorithm 1.

BuildConcept is depicted in detail in FIGS. 3A-3C. The function accepts as inputs S301 a dependency tree, the IRI A identified in step S108, and the knowledge base which it will draw from.

The first step is to call the function getSTY (line 25 of algorithm 1) S302, which obtains the semantic type of IRI A from the knowledge base. This function is a simple SPARQL query over the KB e.g. if a node has already been assigned the IRI of "Malaria" then this function returns the type "Disease" i.e.:

select ?type where {iri bbl:hassTY ?type}

Next the variable n is initialised as 0 S303 and the concept C is initialised with the concept from IRI A 3304. The node provided is selected as the primary node S305.

BuildConcept checks whether the primary node has a child at position n (S306). If yes then child n is selected as the secondary node S307. The linguistic relation between the primary and secondary nodes S308 is considered S309.

If the relation is nominal or modifier term (i.e. "nmod", "npadvmod", "advmod", "obl", "pobj", "dobj", or "nsubj") then the function proceeds to step S331 shown on FIG. 3B via flow connector S310. If the relation is that the label is a verb (i.e. "acl") then the function proceeds to step S361 shown on FIG. 3C via flow connector S311.

Nominal or Modifier Relationship

BuildConcept calls getIRI on the secondary node to obtain the IRI for the label of the secondary node S332 (line 30 of Algorithm 1). The semantic type of that IRI is then obtained via the function getSTY S333 (line 31 of Algorithm 1). BuildConcept then calls the function findRelation S335 (line 32 of algorithm 1) using the semantic types of IRIs A & B and using a set of rules S334 that specify which pairs of semantic types can be linked together with the most probable relation between them in order to guide the selection of IRIs and relations. Examples of these rules that we are using is given in Table 1, below.

TABLE 1

Rules describing which pairs of semantic types can linked and the relations between them.

| Semantic Type | Relation | Semantic Types |
|---|---|---|
| Clinical Finding | Finding Site | Anatomical Structure/Body Part |
| | Associated Morphology | Anatomical Abnormality |
| | Temporal Context | Temporal Concept |
| | Causative Agent | Organism |
| Poisoning | Causative Agent | Food/Substance |
| Anatomical Structure | Laterality | Spatial Concept |

Rules such as these should be ordered according to their frequency of use so at to reduce the time taken to query those rules on average across multiple queries. For example, they could be ordered according to their frequency of appearance in the SNOMED ontology.

Function findRelation picks all the rules of the form <IRI A type, Relation, IRI B type> S334 and then returns the IRI R of the relation from that rule.

For example if a node has been resolved to be a disease then its child nodes are attempted to be resolved with concepts that are of type "Anatomical Structure" or "Body Structure", etc. If the concept IRI that is selected is "Anatomical Structure" then the relation that is picked is findingSite and the constructed concept ∃findingSite.iri.

The concept C is then defined S339 as:

C:=C$\pi$∃R.(B$\pi$BuildConcept(secondary node, B, KB))

Since this definition recursively calls BuildConcept on the secondary node using the IRI B as the second input, the function then proceeds to the secondary node and performs the same function. In this manner, the function proceeds in a depth-first manner down through the dependency tree until the end of the that branch of the dependency tree.

Once the end of the branch is reached and all the children nodes for the selected secondary node have been considered, the function will terminate for the child nodes and fall back to the primary node. BuildConcept can then increment n S314 (FIG. 3A) and can move on to consider child n+1 of the primary node. Of course, if there are branches in the tree below the primary node (i.e. a child node has more than one child) then while that child node will step through values of n while it is considered as the primary node, in order to consider all of that child node's children. As stated above, modern programming languages can take advantage of "for" loops to abstract this process.

Figure 3D:
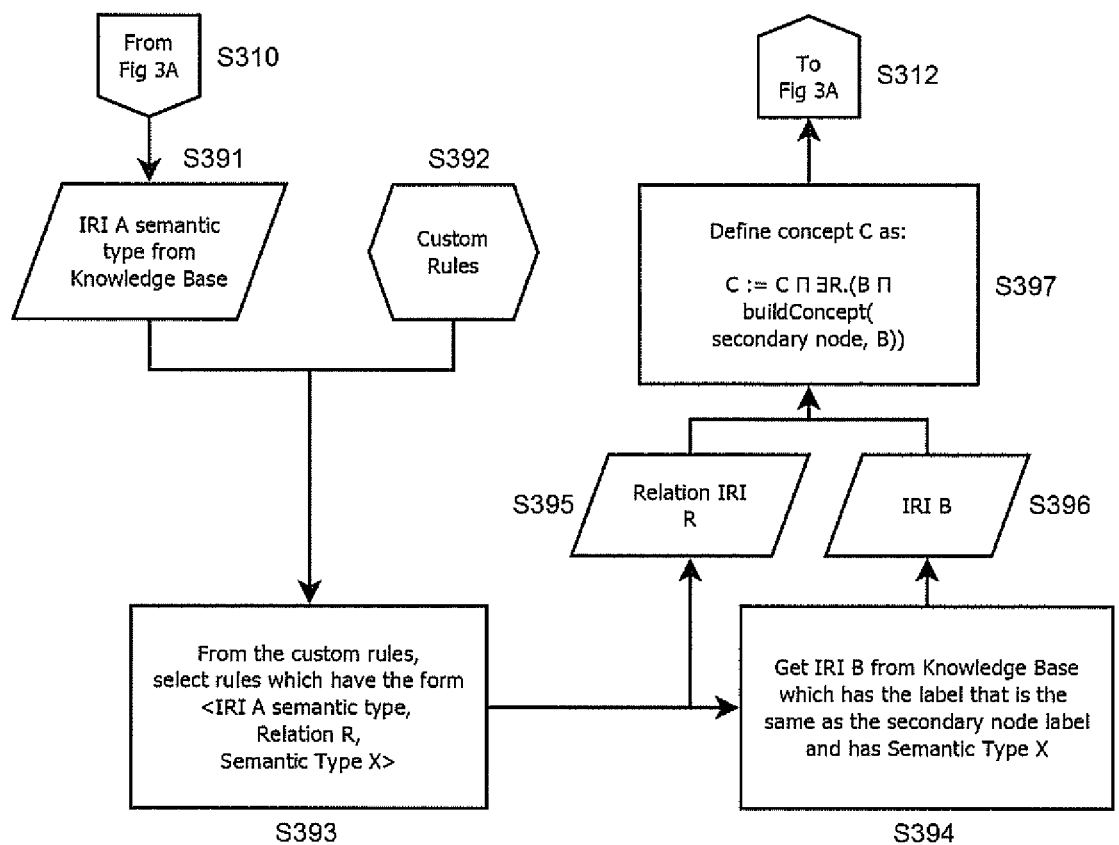
FIG. 3D is a flowchart depicting an alternative variation of the second part of an embodiment of a second processing function which forms part of Algorithm 1.

An alternative variation of this nominal or modier branch of the process is depicted in FIG. 3D. Given the semantic type of the parent node S391 and the custom rules S392, one can select the rules which have the format <IRI A semantic type, Relation R, Semantic Type X> S393 ordered based on likelihood. The IRI B of secondary node can be assumed to have a semantic type (Btype) of one of the values for semantic type X possible within the selected rules. This narrows the search for possible IRIs for the secondary node S394. The relation R S395 and the IRI B S396 can then be used to build a concept S397 in the same manner as shown for the standard variant S339 depicted in FIG. 3B.

Verb Relationship

If the linguistic relation between the primary and secondary node is a verb, i.e. "acl", then the term of the secondary node label actually itself represents the relation that should be used to connect the parent and child concepts.

To achieve this, the function getIRI (as described above) is called on the label of the secondary node S361 to obtain a relation IRI "R" from the knowledge base that matches that label 8363. Function getIRI is then called on the label of first child of the secondary node S362 to obtain a concept IRI "B" S364 from the knowledge base that matches that label.

The concept C is then defined S365 as:

C:=C$\pi$∃R.(B$\pi$BuildConcept(first child of secondary node, B, KB))

As with step S339 in FIG. 3B, it can be seen that this step S365 will also cause the function to proceed recursively down the dependency tree until it reaches the end of that branch of the dependency tree. As with the path shown on FIG. 3B, the function returns to S314 on FIG. 3A and increments n. The function then moves on to consider the next child of the primary node.

Using the dependency tree shown in FIG. 1C which originally derived from the phrase "recent pain provoked by injury", the algorithm will return a concept of the form:

getIRI("Pain")$\pi$∃findRelation(Atype, Btype).getIRI("Recent")$\pi$∃getIRI("Provoked").getIRI("Injury")

where Atype:=getSTY(getIRI("Pain"))={Finding}
and where Btype:=getSTY(getIRI("Recent"))={TemporalConcept}.

Since "provoked" is a verb, it is directly used as a relation, whereas, to connect "Pain" with "Recent" we use findRelation since "Recent" is a modifier.

If the linguistic relation between the primary and secondary node is any other form then that node is simply skipped and the function moves to the next child of the primary node S314, selecting the IRI for each node individually via getIRI. When the conceptBuilder algorithm 1 has considered each node in the dependency tree, the result is the concept C S110, which is then returned S315.

Algorithm 1 Pseudo Code conceptBuilder$_{KB}$(medical phrase)
Root := dependencyParser(phrase)
PreProcess(root)
A := getIRI(KB, root. $\ell$) //ElasticSearch: exact match, pick first IRI
return BuildConcept(root, A)
function PreProcess(node)
    Initialise empty lists newCh and OldCh
    for ch ∈ node.children do
        PreProcess(ch)
        if <node.ch>. $\ell$ ∈ {compound} then //Join compounds
            node. $\ell$ = node. $\ell$ + " " + ch.$\ell$ -continued Algorithm 1 Pseudo Code

```
            Append ch to oldCh and ch.children to newCh
         else if <node,ch>.ℓ ∈ {prep,case} then //Discard function words
            Append ch to oldCh and ch.children to newCh
         end if //otherwise do nothing
      end for
      Remove from node.children all nodes in oldCh and add those in
   newCh
end function
function BuildConcept(node, A)
   Atype := getSTY(A) //select ?type where {A bbl:hasSTY ?type}.
   C := A
   for ch ∈ node.children do
      if <node,ch>. ℓ ∈
      {nmod,npadvmod,advmod,obl,pobj,dobj,nsubj}
   then //nominal or modifier relationship
         B := getIRI(KB,ch. ℓ)
         Btype := getSTY(B)
         R := findRelation(Atype,Btype) //using custom rules
         C := C ⊓ ∃R.(B ⊓ BuildConcept(ch,B))
      else if <node,ch>.ℓ == acl then //verb relationship
         R := getIRI(KB,ch. ℓ)
         B := getIRI(KB, ch.children[0]. ℓ)
         C := C ⊓ ∃R.(B ⊓ BuildConcept(ch.children[0],B))
      end if
   end for
   return C
end function
```

Algorithm 2—Reasoning with Textual Knowledge

Based on the concept builder (Algorithm 1), a subsumption checking algorithm is presented that given two concepts, it can exploit both the ontological axioms as well as their textual information in order to compare them.

Example 1—Application of conceptBuilder( )

Consider the SNOMED ontology $\mathcal{O}$ and the concept "recent head injury". This concept can be represented in two different ways as follows:
$C_1$:=RecentInjury⊓∃findingSite.Head
$C_2$::
  =Injury⊓∃findingSite.Head⊓∃temporalContext.Recently Although these two concepts capture the same real-world notion, it can be verified using a reasoner such as ELK that $\mathcal{O} \not\models C_1 \sqsubseteq C_2$ and $\mathcal{O} \not\models C_2 \sqsubseteq C_1$ since, in SNOMED, Recentinjury is not a sub-class of Injury.

Nevertheless, if RecentInjury in $C_1$ is replaced with the output of concept builder applied on its label (i.e. on "Recent Injury") the following concept is obtained:
$C_1'$:=Injury⊓∃temporalContext.Recently⊓∃findsite.Head Then $\mathcal{O} \models C_1' \sqsubseteq C_2$ and $\mathcal{O} \models C_2 \sqsubseteq C_1'$ is achieved as desired. The above example suggests demonstrates that the concept builder can be used to extract possible "missing" formal definitions from the textual data.

However, since concept builder is based on statistical techniques its use may lead to errors. On the one hand, by wrongly assigning an IRI to a term it may lead to false positives and, on the other hand, excessive use can introduce noise and prevent a desirable subsumption fom being discovered as the following example shows.

Example 2—Inappropriate Use of conceptBuilder( )

Considering again concepts $C_1$ and $C_2$ from Example 1. Assume, in addition, that the concept builder is also applied to the label of concept Injury replacing this conjunct in $C_2$ with concept builder proposed definition. The label of this concept in SNOMED is "Traumatic AND/OR non-traumatic injury" and this approach will create $C_2'$ that in addition contains ∃Interprets.Traumatic⊓∃AssociatedWith.Non-traumatic. Then $\mathcal{O} \not\models C_1 \sqsubseteq C_2$ is achieved. Similarly, it is possible to encounter cases where the concept builder should be applied to the candidate subsumer $C_2$ but not on the (candidate) subsumee $C_1$.

The above examples show that in an embodiment, the conceptBuilder should not be applied "exhaustively" on the label of both input concepts. Indeed the subsumption algorithm depicted in Algorithm 2 couples an OWL reasoner with concept builder in a carefully designed way to control the application of the NLP module and avoid applying it when it assesses that it would not lead to positive results.

Figure 4A:
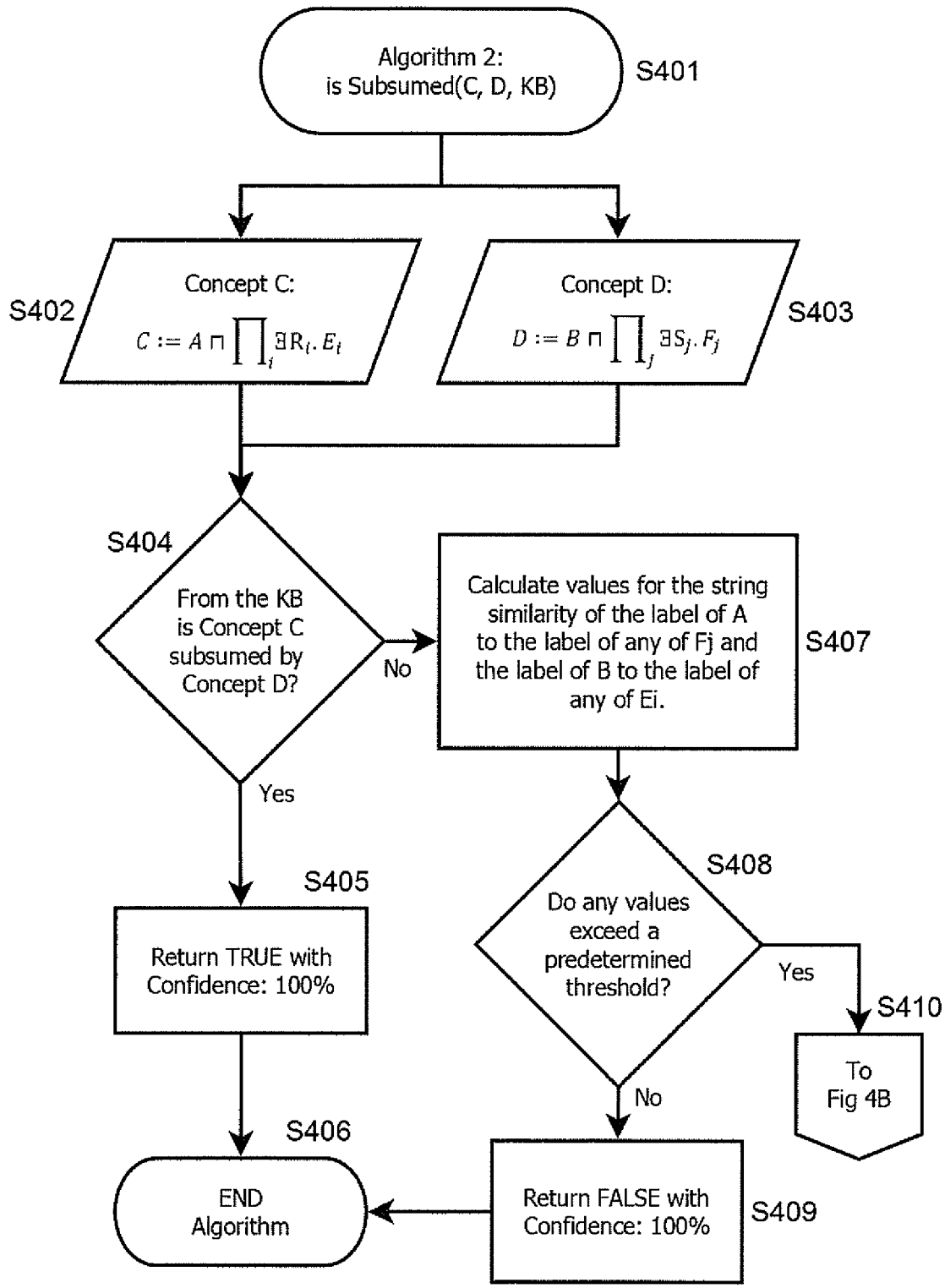
FIG. 4A is a flowchart depicting the first part of an embodiment of Algorithm 2.
Figure 4B:
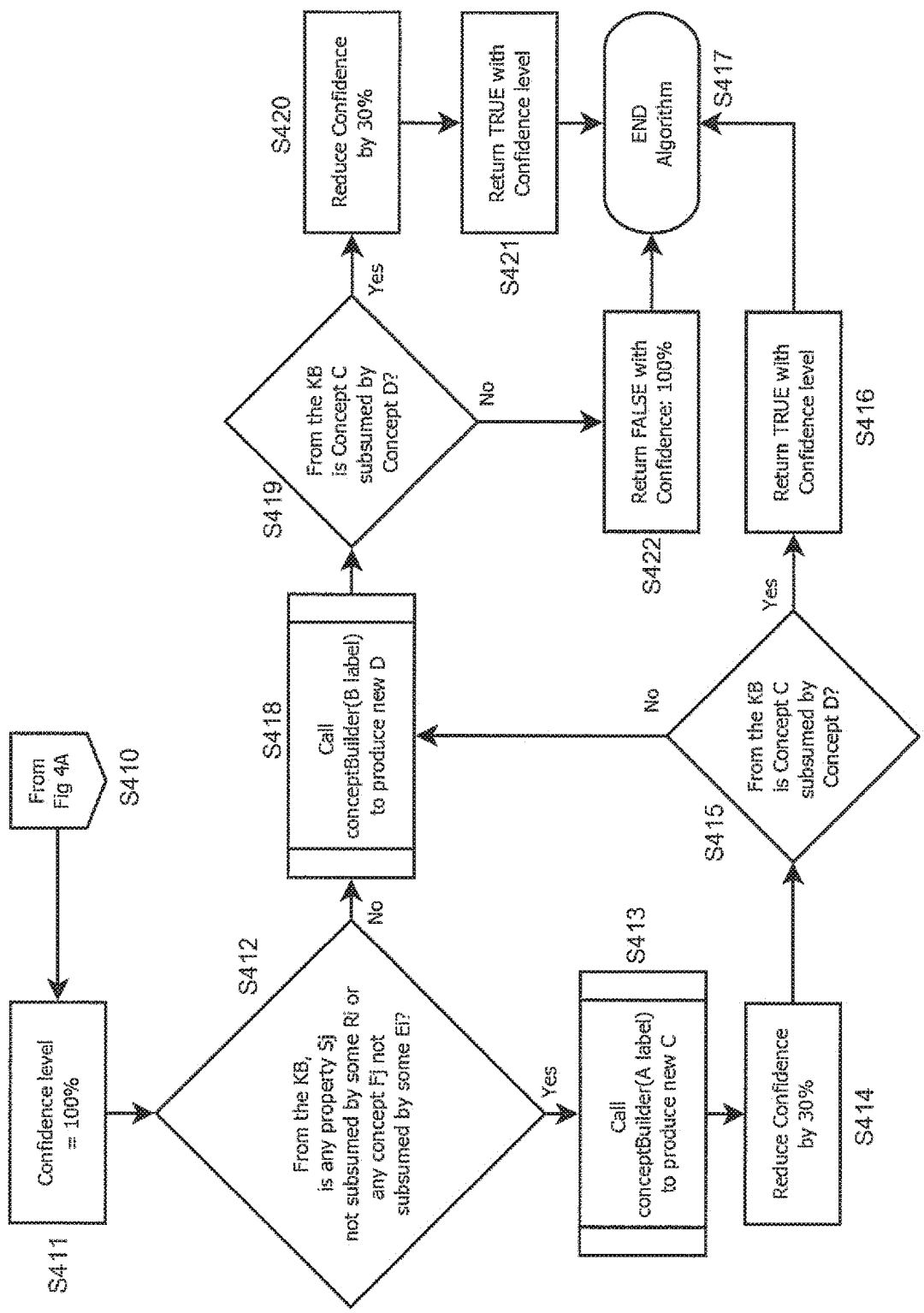
FIG. 4B is a flowchart depicting the second part of an embodiment of Algorithm 2.

In more detail as shown in FIGS. 4A-4B, given a candidate subsumption C⊑D S402, S403 the algorithm first attempts to check if it is entailed using a standard OWL reasoner S404. If the reasoner replies positively then the subsumption is guaranteed to hold and the algorithm returns TRUE with a confidence of 1.0 (100%) S405. It is to be understood that any sufficiently high confidence may be used as an output to match the concepts or subsumption is question. It may be preferred that the confidence is any value from: 99%, 98%, 97%, 96%, 95%, 94%, 93%, 92%, 91%, 90%, 85%, 80%, 75%, or any value therebetween.

If the OWL reasoner returns false, then the algorithm proceeds to use a heuristic method via the proceedToBuilder function S407, to check whether to proceed to using the concept builder on the labels of C and/or D.

Example 3—Subsumption Checking

The knowledge base can be expressed using $\varepsilon\mathcal{L}$ concepts and axioms and, moreover, conceptBuilder produces $\varepsilon\mathcal{L}$ concepts, hence it is possible to use efficient OWL reasoners like ELK to check for entailments and compare concept with respect to subsumption. However, in an embodiment, the knowledge base is very large, further, the complexity of the inference rules that these systems internally use do not scale Consequently, in an embodiment, the knowledge base is loaded to the GraphDB triple-store. GraphDB is one commercially available triple-store with good performance and scalability guarantees, however, other triple-stores also exist and can be used. GraphDB's efficiency stems from the fact that it implements a weak set of inference rules, consequently, the system will not be accurately compare the concepts computed by conceptBuilder function.

To overcome this issue, in an embodiment, method of the invention includes a lightweight but approximate OWL reasoner which implements some additional consequence-based reasoning functionality on top of GraphDB using SPARQL queries. The SPARQL queries that are described below permit the simulation of some of the inference that a complete $\varepsilon\mathcal{L}$ reasoner will perform over a knowledge base, but it performs this up to a certain level hence avoiding the aforementioned scalability issues.

Consider a patient with a face injury represented in his record using the SNOMED concept FaceInjury. Assume now that after analysing user text in the chatbot the concept Injury⊓∃findingSite.HeadStructure has been produced. Subsequently, the concepts, FaceInjury and Injury⊓∃findingSite.HeadStructure are compared with respect to subsumption; i.e., it is required to check: FaceInjury⊑Injury⊓∃findingSite.HeadStructure SNOMED contains the axioms FaceInjury⊑∃findingSite.FaceStructure and FaceStructure⊑HeadStructure, hence the subsumption relation between these two concepts holds. A system like ELK is able to answer positively about the entailment of this subsumption relation, however, GraphDB will not since its internal set of inference rules cannot handle concepts of the form ∃findingSite.FaceStructure. This example demonstrates an entailment that triple-stores cannot identify.

In order to provide some level of expressive reasoning, the method of this embodiment makes use of "concept expansion" prior to performing the subsumption check S404. The concept expansion is omitted from the Figures for the sake of readability. This approach is defined in detail below.

Let concepts C and D be defined as follows: Definition 1:
$C := A \sqcap \Pi_{i=1}^{m} \exists R_i . E_i$
$D := B \sqcap \Pi_{j=1}^{n} \exists S_j . F_j$
And let Function expandCon(C) be defined as $$C_{ex} := A \sqcap \prod_{i=1}^{m} \exists R_i \cdot E_i \prod_{k=m+1}^{q} \exists r_k \cdot filler_k$$

where each $r_k$ and $filler_k$ is taken by the results of the following SPARQL query over some KB:
select ?r ?filler where {: c₁ ?r ?filler. ?r a owl: objectProperty.}

This query will search the knowledge base for axioms which match the format of C₁ [relation] [concept]. As mentioned above, SNOMED contains the axiom FaceInjury ⊑ ∃findingSite.FaceStructure. Since this axiom contains C (FaceInjury), a relation (findingSite) and a further concept (FaceStructure), this axiom will be one of the results returned by the SPARQL query. $C_{ex}$ in this example could therefore be defined as:
$C_{ex}$=FaceInjury⊓∃findingSite.FaceStructure By using "concept expansion", the algorithm can provide a greater level of expressive reasoning than is available through a typical triple-store deterministic reasoner while not requiring the demanding computational resources required by traditional expressive reasoning algorithms.

Then, subsumption between the concepts can be identified using the following function: Function isSubSet(C; D) returns true iff the following tests hold, otherwise it returns false:

1. query ask where {: A rdfs:subClassOf : B .} returns true.
2. for every j∈[1; n] there exists i∈ [1; q] s.t. the following query returns true:
    ask where {: $R_i$ rdfs:subClassOf : $S_j$ .: $E_i$ rdfs:subClassOf : $F_j$ .}

This query first whether that part A of concept C is subsumed by part B of concept D. The query also checks whether each property $R_i$ to see if it subsumed by any property $S_j$ and checks each concept $E_i$ to see if it subsumed by any concept $F_j$. This can be a indirect subsumption and still hold true e.g. A⊑X⊑B⊨A⊑B. Provided that all of these conditions are satisfied (i.e. A⊑B, each $R_i$ subsumed by some $S_j$, each $E_i$ subsumed by some $F_j$), then the query will return true and there it can be concluded that there is a subsumption relationship.

Example 4—String Similarity

As mentioned above, in some embodiments, conceptBuilder should not be used. For example, if the subsumption FootPain⊑HeadInjury is being tested then it is intuitively clear that there is no need to proceed into analysing the text of either of these concepts and using conceptBuilder bears the danger of leading to a false positive subsumption.

In order for the computer implemented method of the invention to consider whether it should proceed with using conceptBuilder, using the concepts from definition 1 above, the function proceedToBuilder (line 10 of algorithm 2) S407 returns TRUE when applied on C and D if the following condition is satisfied:

For A (resp. B) there exists some ∃$S_j$.$F_j$ (resp. ∃$R_i$.$E_i$) such that for l the label of A (resp. B) and for ε the label of $F_j$ (resp. $E_i$) there exists sim(l,ε)≥T, where sim( ) is some string similarity algorithm and T some threshold.

This can be interpreted as checking the similarity between the label of A with the labels of $F_j$, and the label of B with the labels of $E_i$ S407, to see if any of the comparisons return a similarity score above a predetermined threshold S408.

For example for the labels of the concepts in the (candidate) subsumption FootPain⊑RecentInjury, most string similarity measures like Levenshtein distance, Needleman-Wunch, and Smith-Waterman return a similarity score between 0.09 and 0.5 (a low degree). The threshold will not be exceeded and so the similarity of the two concepts being compared is too low. As such the risk of generating a false-positive from the use of conceptBuilder is too high to proceed. Instead the algorithm returns FALSE and a confidence of 1.0 (100%) or thereabouts (S409).

In contrast, for the case of the concepts from Example 1 comparing the label of RecentInjury with that of concept Recently using the above three string similarity metrics returns a similarity score between 0.54 and 0.75 (a high degree) due to the conjunct ∃temporalContext.Recently. In that case, the algorithm would proceed to steps that would make use of the conceptBuilder (S411 on FIG. 4B).

Example 5—analyseSubsumeesLabel( )

The next step of Algorithm 2 is to determine which concepts, either C or D, to apply the conceptbuilder to. This check is performed by the function analyseSubsumeesLabel$_{KB}$( ) (line 16, S413).

analyseSubsumeesLabel( ) works by checking if the following condition is satisfied based on concepts C and D as defined above, when provided with a knowledge base:

result = true if for every j∈[1; n] there exists i∈ [1; q] s.t. the following query returns true:
    ask where {: $R_i$ rdfs:subClassOf : $S_j$ .: $E_i$ rdfs:subClassOf : $F_j$ .}
return !result This query is the same test used in point 2 of the isSubSet ( ) function described on paragraph [0149], except that when the query returns true, the function returns false and vice versa. It should be noted that if the isSubSet( ) query above fails on point 1 (i.e. A is not subsumed by B) but point 2 holds true (there is subsumption between the other concepts of C and D), then conceptBuilder( ) should be performed on the label B from concept D instead of label A from concept C, as it is more likely that expanding concept B will lead to a positive subsumption result.

Considering again the two concepts $C_1$ and $C_2$ from Example 1:
$C_1$:=RecentInjury⊓∃findingSite.Head
$C_2$::=
    Injury⊓∃findingSite.Head⊓∃temporalContext.Recently ∃temporalContext.Recently is not subsumed by any conjunct of similar form in $C_1$. Even if expandCon( ) is applied on $C_1$, no conjunct is added. Hence, analyseSubsumeesLabel($C_1$,$C_2$) would return TRUE and proceed to use the conceptBuilder on the label of RecentInjury (line 17, S414).

In contrast, analyseSubsumeesLabel($C_2$,$C_1$) returns FALSE as for all of the conjuncts of the form ∃R.E in C, there is a conjunct of the same form in $C_2$ that subsumes it, i.e. ∃findingSite.Head is present in both C, and $C_2$. As a result, the algorithm instead skips lines 17-23 and instead runs the concept builder on the label of Injury (line 24, S418).

Example 6—Further Use of conceptBuilder( )

Presuming that analyseSubsumeesLabel( ) returns TRUE (line 16, S412) and the conceptBuilder is applied to Concept C (line 17, S413), the algorithm is tracking a confidence level which is initialised at 100% (line 14, S411). After conceptBuilder has generated new concept C, the confidence level is reduced to a lower amount, e.g. it is reduced by 30% (line 18, S414). This reflects the concern that using the conceptBuilder increases the risk of a false positive result.

The subsumption between the revised concept C and the concept D is then checked (line 19, S415). If the subsumption is now true, the algorithm returns TRUE with current confidence level (e.g. 70%) (line 20, S416).

If however the subsumption is still not true, then conceptBuilder is applied to Concept D (line 24, S418).

The subsumption between the revised concept C and the revised concept D is then checked (line 25, S419). If the subsumption is now true, the confidence level is further reduced (e.g. by a further 30%)(S420). The further use of conceptBuilder leads to an even greater risk of false positive, hence a low confidence level is given. The algorithm then returns TRUE with current confidence level (e.g. 40%) (line 26, S421).

If however the subsumption is still not true, then the algorithm returns FALSE with 100% (or thereabouts) confidence level (line 29, S422). As the algorithm is unable to resolve any subsumption after the application of conceptBuilder to both concept C and D, it is assumed that there is no subsumption of C by D.

Returning to the analyseSubsumeesLabel( ) check (line 16, S412). If this function instead returns FALSE, then it is not appropriate to apply conceptBuilder to concept C (lines 17-24 are skipped) and instead, since it has already been determined that concept C is not subsumed by D (line 6, S404), conceptBuilder is applied only to D (line 24, S418). Once conceptBuilder is applied to concept D, the confidence level is reduced (e.g. to 70%).

The subsumption of the concept C by the revised concept D is checked (line 25, S419). If the subsumption is now true, the confidence level is reduced (e.g. by 30%)(S420) for the same reasons as given above. The algorithm then returns TRUE with current confidence level (e.g. 70%) (line 26, S421).

If however the subsumption is still not true, then the algorithm returns FALSE with 100% (or thereabouts) confidence level (line 29, S422). As the algorithm is unable to resolve any subsumption after determining that it is inappropriate to apply conceptBuilder to concept C and applying it only to concept D, it is assumed that there is no subsumption of C by D.

The end output of Algorithm 2 is a Boolean (TRUE or FALSE) result representing whether C is subsumed by D and an outputted value representing the confidence level in that subsumption result.

| Algorithm 2 Pseudocode |
|---|
| isSubSumed$_{KB}$(C,D) |
| wherein C and D are concepts of the form: |
| C := A π $\Pi_i \exists R_i.E_i$ and D := B π; $\Pi_j \exists S_j.F_j$ |
| if KB ⊨ C ⊑ D then        //isSubSet( ) |
|     return <true,1.0> |
| end if |
| if !proceedToBuilder$_{KB}$(C,D) then |
|     return <false,1.0> |
| end if |
| $C_{br}$ := C |
| d := 1.0 |
| if analyseSubsumeesLabel$_{KB}$(C,D) then |
|     $C_{br}$ := conceptBuilder$_{KB}$(A.label) π $\Pi_i \exists R_i.E_i$ |
|     d := d − 0.3 |
|     if KB ⊨ $C_{br}$ ⊑ D then |
|         return <true,d> |
|     end if |
| end if |
| $D_{br}$ := conceptBuilder$_{KB}$(B.label) π $\Pi_j \exists S_j.F_j$ |
| if KB ⊨ $C_{br}$ ⊑ $D_{br}$ then |
|     return <true, d − 0.3> |
| end if |
| return <false,1.0> |

Evaluation

We conducted an experimental evaluation of our designed algorithms using the Babylon Knowledge Base and a real use case. In our first evaluation we randomly picked 200 concepts from the SNOMED ontology which have a label that contains at least two words and used concept builder to construct a concept definition. Out of the 200 concepts, concept builder failed to build a concept in 19 cases (9.5%) and the reason was that it was not able to assign an IRI to some of the words in the medical phrase.

For example, we could not find IRIs in the knowledge base for words "Ionizing" and "Psychoactive". For the remaining 181 concepts we asked an in-house doctor to evaluate their quality using one of the labels wrong, correct, or partially correct. They identified 21 wrong concepts, 108 correct concepts, and 52 partially correct concepts. The median concept builder time to construct a concept was 354 milliseconds, starting with a cold cache.

TABLE 2

Examples of correct, wrong, and partially correct concept definitions

| Concepts marked correct | |
|---|---|
| Infestation by Phthirus | Infestation Π ∃assocWith.Phthirus |
| Acute Myocardial Infarction | Infarction Π ∃tempCtx.Acute Π ∃findingSite.Myocardial |
| Coronary Artery Thrombosis | ArteryThrombosis Π ∃assocWith.Coronary |
| Concepts marked wrong | |
| Prune belly syndrome | Prune Π ∃assocWith.Syndrome Π ∃findingSite.Belly PruneBellySyndrome (doctor concept) |
| Bladder inertia | BladderInertia Inertia Π ∃findingSite.Bladder (doctor concept) |

TABLE 2-continued

Examples of correct, wrong, and partially correct concept definitions

| Concepts marked partially correct | |
|---|---|
| Blood in urine | Blood ⊓ ∃assocWith.Urine<br>Blood ⊓ ∃findingSite. Urine<br>(doctor concept) |
| Carpal tunnel syndrome | Syndrome ⊓ ∃Interprets.Tunnel ⊓<br>∃assocWith.Carpal<br>Syndrome ⊓<br>∃findingSite.CarpalTunnel<br>(doctor concept) |

Table 2 presents some representative examples of concepts from these three categories, their text label used by conceptBuilder, the constructed concept definition and, where the doctor did not mark the constructed concept as correct, the correct one proposed by the doctor.

Cases of (partial) failure were due to either too aggressive NLP analysis that split the phrase into too many tokens or where NLP was conservative and no concept definition was constructed or a wrong choice of a relation. Arguably, this latter problem is the most difficult to resolve in this evaluation scenario since in most cases relations do not exist as verbs in the text but they need to be inferred.

As a second experiment, we asked our doctors to produce a list of 100 pairs of medical concepts (described as medical phrases) that do not exist in SNOMED and according to them are related with subsumption. We then used conceptBuilder to extract formal definitions for them and the reasoner to compare them.

Our goal is to simulate the scenario where knowledge is communicated mostly in textual form and our techniques can be used to formally compare their intended (hidden) meaning. Out of 100 pairs, reasoner (algorithm 2) returned TRUE in 54 cases (54%). Obviously, in order for the reasoner to return TRUE both of the following conditions must hold: dependency parsing must build "similar" trees for both phrases and the knowledge base concepts associated to the nodes of the tree need to participate in a subsumption relation.

For example, in the pair <"Possible Neck Wound", "Possible Injury">, "Wound" and "Injury" are mapped to respective SNOMED concepts, the former is subsumed by the latter, and dependency parsing puts both of them as roots. Examples of failures are given in Table 3 below, where we present the doctor medical phases and the concepts passed concept reasoner.

In many of these cases the builder and the reasoner behaved well in the sense that they mapped words in text to concepts that seemed to be semantically related but either our KB or our initial data sources are missing subsumption relationships between the chosen concepts. For instance, in the first example in the table, the word "Treatment" is once mapped to a concept from the LOINC ontology whereas in the other to a concept from HL7 and no (equivalent) mapping between them exists in our KB hence reasoner returns FALSE. Similarly no mapping between "Egg hypersensitivity" from MeSH and "Allergy" from SNOMED exists in our KB hence reasoner cannot properly compare these concepts. Interestingly we also encountered cases that it looked as if SNOMED is missing a valid subsumption relation, like between KneeReplacement and Replacement. However, most cases that conceptReasoner returned FALSE (almost 70%) were due to either words in text that were mapped to unrelated concepts from the KB, language difficulties or differently structured dependency trees.

TABLE 3

Example of pairs of concepts for which concept reasoner returns FALSE

| Correctly parsed but missing semantic relations | |
|---|---|
| Certain treatments<br>Inc: Treatments ⊓<br>associatedWith.Certain | Any treatment<br>HI7: Treatment |
| Egg hypersensitivity<br>mesh: EggHypersensitivity | Allergy<br>snmd: Allergy |
| Knee replacement<br>KneeReplacement | Joint replacement<br>Replacement ⊓<br>∃associatedWith.Joint |
| Language difficulties - dependency tree incompatibilities | |
| Liver transplant rejection<br>TransplantRejection ⊓<br>∃findingSite.Liver | Transplant complication<br>Complication ⊓<br>∃findingSite.Transplant |
| Seasonal depression<br>Depression ⊓ ∃temportalCtx.Seasonal | Mood disorder<br>Disorder ⊓ ∃interprets.Mood |
| Streptococcal sore throat<br>Throat ⊓<br>∃associatedWith.Streptococcal ⊓<br>∃associatedWith.Sore | Bacterial infection<br>Infection ⊓ ∃interprets.Bacterial |

Finally we turned our attention to one of babylon's use cases—that is, the migration of UMLS concepts to SNOMED. We obtained 1176 UMLS concepts together with their labels (label$_i$) which doctors used to perform the migration as well as the SNOMED concept $C_i^d$ that they proposed. We applied concept builder on each label to automatically construct a proposed SNOMED concept $D_i$ and then called concept reasoner twice to check if $D_i \sqsubseteq C_i^d$ and $C_i^d \sqsubseteq D_i$. Our results are summarised in Table 4 below. We distinguish between cases that doctors were able to directly map a UMLS concept to a single SNOMED IRI (called simple concepts in the table) and those for which they had to construct a complex concept combining various SNOMED ones. Columns "equivalent" and "subsumed" denote cases where both or one of the call to the reasoner returned TRUE, respectively. "t.o." represents how many cases concept reasoner did not manage to return within a timeout of 5 seconds, which the numbers in the parenthesis shown in how many of those calls the reasoner succeeded by a simple subsumption call to GraphDB, by also using method expandCon( ) and by having to employ concept builder internally.

TABLE 4

Results of concept builder vs. doctor's concepts using concept reasoner

| | Total | Equivalent | Subsumed | t.o. |
|---|---|---|---|---|
| Complex concepts | 203 | 89 (0/82/96) | 8 (0/4/4) | 6 |
| Simple concepts | 973 | 731 (338/219/905) | 111 (8/34/69) | 27 |

Our results on complex concepts are to a large extent consistent with the results shown in Table 3, although here it is much harder to match the concept that was originally built by the doctors. This is because in many cases doctors pick concepts from SNOMED whose label may significantly differ from the words that appear in the original UMLS concept label. For example, for label "Acoustic neuroma"

doctors interpreted the word "Acoustic" with the concept "AcousticNerve" whereas concept builder picked concept "Acoustic".

Interestingly, function expandCon( ) has a significant impact in increasing the inference power on top of GraphDB and determining subsumption without needing to call concept builder. As this method is also logic-based in all these cases, concept reasoner returns TRUE with 100% confidence. Moreover, since logic-based methods are sound all cases that reasoner returned TRUE by only relying on them imply that indeed the concepts constructed by concept builder are equivalent to the doctor defined one. For the cases that concept reasoner employed concept builder internally a manual sample-based verification using doctors had to be conducted and led to the same accuracy results as in our first experiment, The case of simple concepts is obviously significantly easier and it is interesting to notice that reasoner is calling concept builder in far more cases since doctors had not "decomposed" the original concepts at all but mapped them to a single SNOMED IRI.

Related Work and Conclusions

There are many approaches for learning OWL ontologies from instance data or text. In all previous works the authors worked on full sentences that necessarily contained verbs and which are also assumed to have a "definitory" character, e.g. "Enzymes are proteins that catalyse chemical reactions". In such cases, verbs can be used as relations between the medical terms and the definitorial nature of sentences brings them already too close to the structure of OWL concepts.

In constract, the method of the invention helps to solve the problem of extracting concepts definitions from noun phrases which is considerably more challenging since these are usually small and don't contain verbs, e.g. "severe pain" instead of "severe pain caused by car accident". To achieve this we use dependency parsing to extract phrase subunits and we infer the relation between by exploiting semantic types, ontological knowledge (domain/range restrictions and property usage) and statistical information from the usage of relations in SNOMED. Semantic type information is also used to better map text token to KB concepts.

In addition, the method of the invention includes a concept subsumption checking algorithm that tries to exploit both logical and textual information to determine semantic relations between concepts. Our algorithm combines logic-based and NLP-based techniques in a carefully engineered way in order to reduce false-positives caused by statistical techniques. To the best of our knowledge, no similar reasoning system exists in the literature.

Figure 5:
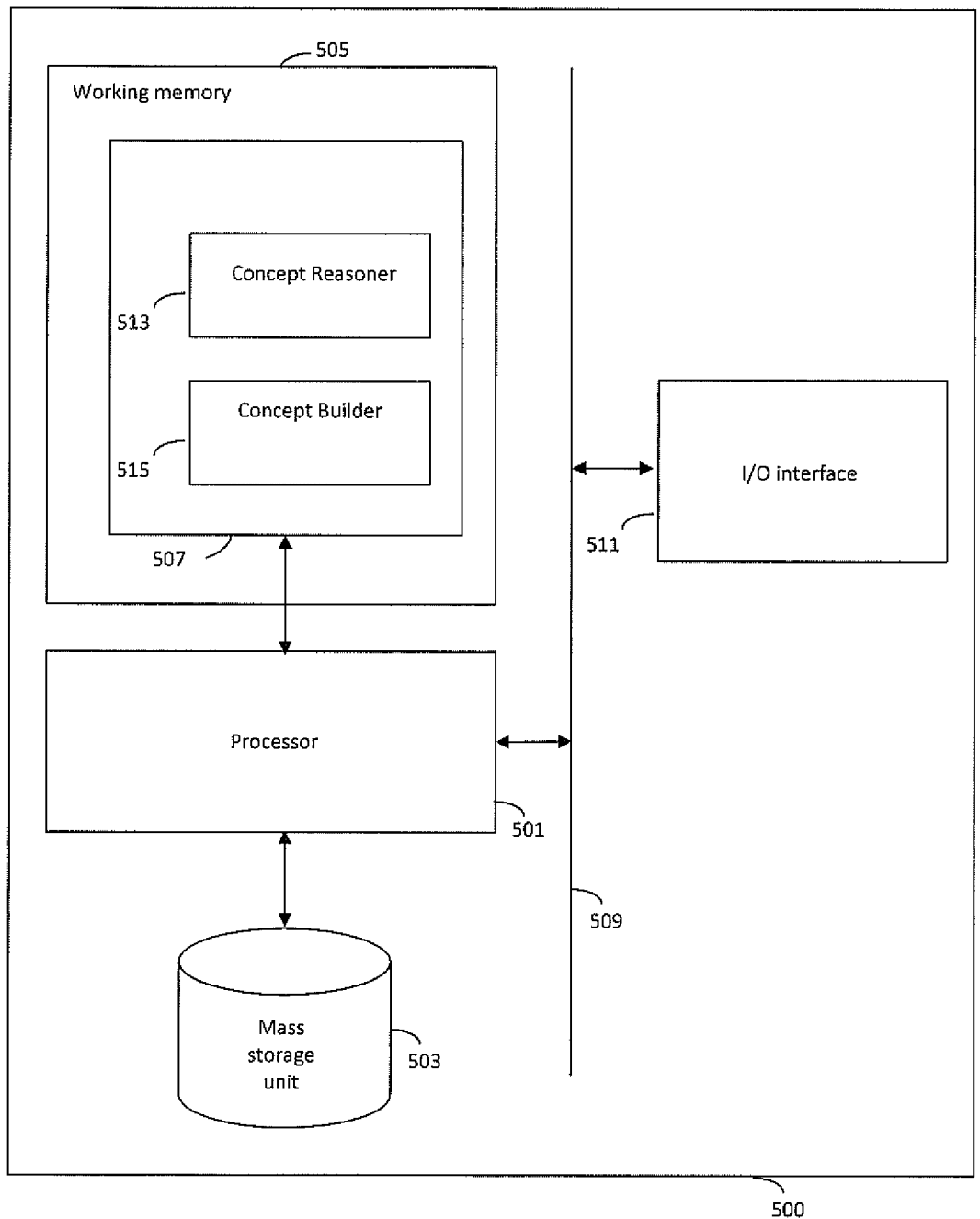
FIG. 5 is a simplified diagram of a computer.

While it will appreciate that the above embodiments are applicable to any computing system, an example computing system is illustrated in FIG. 5, which provides means capable of putting an embodiment, as described herein, into effect. As illustrated, the computing system 500 comprises a processor 501 coupled to a mass storage unit 503 and accessing a working memory 505. As illustrated, a concept reasoner 513 and concept builder 515 are represented as software products stored in working memory 505. However, it will be appreciated that elements of the concept reasoner and/or concept builder may, for convenience, be stored in the mass storage unit 503.

Usual procedures for the loading of software into memory and the storage of data in the mass storage unit 503 apply. The processor 501 also accesses, via bus 509, an input/output interface 511 that is configured to receive data from and output data to an external system (e.g. an external network or a user input or output device). The input/output interface 511 may be a single component or may be divided into a separate input interface and a separate output interface.

Thus, execution of the concept reasoner and/or concept builder by the processor 501 will cause embodiments as described herein to be implemented.

The concept reasoner and/or concept builder can be embedded in original equipment, or can be provided, as a whole or in part, after manufacture. For instance, the concept reasoner and/or concept builder software 507 can be introduced, as a whole, as a computer program product, which may be in the form of a download, or to be introduced via a computer program storage medium, such as an optical disk. Alternatively, modifications to existing concept reasoner and/or concept builder software can be made by an update, or plug-in, to provide features of the above described embodiment.

The computing system 500 may be an end-user system that receives inputs from a user (e.g. via a keyboard) and determines similarity values (e.g. for determining a response to a query). Alternatively, the system may be a server that receives input over a network and determines the similarity values. Either way, these similarity values may be used to determine appropriate responses to user queries, as discussed with regard to FIG. 1.

For instance, the mass storage unit may store predefined phrases, and the system may be configured to determine similarity values with respect to an input phrase relative to each of the predefined phrases. The system may then be able to determine the most similar predefined phrase and then respond with a predefined response that is associated with that predefined phrase. The predefined phrases may be stored as sets of embedding vectors.

Accordingly, by providing more accurate and efficient means of determining the similarity between sets of words, the embodiments described herein provide improvements in natural language processing that, for instance, can improve the accuracy and efficiency of artificial conversational entities.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

While certain arrangements have been described, the arrangements have been presented by way of example only, and are not intended to limit the scope of protection. The inventive concepts described herein may be implemented in a variety of other forms. In addition, various omissions, substitutions and changes to the specific implementations described herein may be made without departing from the scope of protection defined in the following claims.

The invention claimed is:

1. A text processing method for improving the accuracy of a response to a query directed to a system comprising concepts and relations defined by a knowledge base, wherein the method comprises:
    producing a dependency tree from the query, wherein the dependency tree has at least one branch containing nodes and at least one connection between those nodes, wherein each node has a node label which represents a term within the query, and wherein each connection has a label which represents the linguistic relationship between terms within the query;
    from the dependency tree, generating a query concept using concepts and relations defined by the knowledge base;
    checking if the query concept has a subsumption relationship with a candidate concept retrieved from the system, and if no subsumption relationship is initially identified, optimising the dependency tree by changing the nodes, followed by repeating the generating and the checking,
    wherein the query concept and the candidate concept comprise at least one atomic concept; and
    outputting the response to the query based on the dependency tree and the query concept.

2. The method according to claim 1, wherein the system is a diagnostic engine or a medical records system.

3. The method according to claim 1, wherein the query concept and/or candidate concept is a complex concept comprising more than one atomic concept.

4. The method according to claim 1, wherein the changing of nodes comprises the merging and/or deletion of nodes.

5. The method according to claim 1, wherein the optimisation of the dependency tree uses the linguistic relationship between terms to decide whether to change the nodes.

6. The method according to claim 5, wherein if the linguistic relationship between some terms is that the terms form part of a multi-word expression, the nodes with labels representing those terms are merged.

7. The method according to claim 5, wherein if the linguistic relationship between some terms is that a term is a preposition or case, then the node with the label representing that term is deleted.

8. The method according to claim 5, wherein the optimisation of nodes comprises the following steps:
    selecting a primary node;
    for each child of the primary node:
        selecting that child node as the secondary node;
        recursively performing this optimisation process on the secondary node so that the optimisation process begins at the end of a branch of the dependency tree;
        if the linguistic relationship is that the terms represented by the labels of the primary and secondary nodes form part of a multi-word expression, then the primary and secondary node are merged;
        if the linguistic relationship between some terms is that a term is a preposition or case, then the node representing that term is deleted;
        if the secondary node is merged or deleted, attaching the children of the secondary node to the primary node.

9. The method according to claim 1, wherein the optimisation of nodes further comprises selecting a sequence of nodes, joining together the labels of those nodes in different combinations to form a chunked label, comparing the chunked label to concepts defined by a knowledge base, and if a matching concept is found, merging the nodes representing those terms into a single chunked node having the chunked label as the label for the chunked node.

10. The method according to claim 1, during the generation of the query concept, the linguistic relationship between terms determines how to select concepts and relations defined by the knowledge base for use in the query concept.

11. The method according to claim 10, wherein if the linguistic relationship between some terms is that one of the terms is a nominal or modifier, performing the following steps:
    from the terms, selecting concepts based on the labels of the nodes representing those terms;
    identifying semantic types of the concepts;
    from the semantic types, selecting the most likely relation between those types;
    appending the relation and concepts to the query concept.

12. The method according to claim 10, wherein if the linguistic relationship between some terms is that two or more non-verb terms are linked by a verb term, performing the following steps:
    selecting concepts based on the non-verb node labels;
    selecting a relation based on the verb node label;
    appending the relation and concepts to the query concept.

13. The method according to claim 10, wherein the generation of the query concept comprises the following steps:
    selecting a node as a primary node;
    selecting a first concept based on the label of the primary node;
    obtaining the semantic type of the first concept;
    initially defining the query concept as the first concept;
    for each child node of the primary node:
        selecting that child node as the secondary node;
        if the linguistic relationship is such that term represented by the label of the secondary node is a nominal or modifier:
            selecting a second concept based on the label of the secondary node;
            obtaining the semantic type of the second concept;
            choosing the most likely relation based on the semantic types of the first and second concept;
            appending the relation and the second concept to query concept;
            recursively performing this query concept generation process on the secondary node, selecting the secondary node as the primary node in the selecting the node as the primary node, such that the concepts and relations subsequently identified are appended to query concept;
        if the linguistic relationship is that the term represented by the label of the secondary node is a verb:
            selecting a relation based on the label of the secondary node;
            selecting a second concept based on the label of the first child of the secondary node;
            appending the relation and the second concept to the query concept;

recursively performing this query concept generation process on the first child of the secondary node, selecting the first child of the secondary node as the primary node in the selecting the node as the primary node, such that the concepts and relations subsequently identified are appended to the query concept and returning the query concept.

14. The method according to claim 1, wherein the checking for a subsumption relationship comprises:
determining if the first concept of the query concept is subsumed by the first concept of the candidate concept;
determining whether for each relation in the query concept, there is a relation in the candidate concept that subsumes it, and for each concept in the query concept there is a concept in the candidate concept that subsumes it.

15. The method according to claim 1, wherein the checking for a subsumption relationship further comprises:
choosing an axiom from the knowledge base with a structure: concept-relation-concept, wherein the first concept of the axiom corresponds to a concept from the query concept;
using the axiom in place of the concept from the query concept when checking the subsumption relationship.

16. The method according to claim 1, wherein the checking further comprises additional comparisons between the query concept and the candidate concept and the results of these comparisons are used to decide whether to further optimise the dependency tree, wherein the additional comparisons comprise calculating a score for the similarity between a label of the query concept and a label of the candidate concept and wherein if the score for the similarity is below a predetermined threshold, the step of optimising the dependency tree is not performed and it is determined that there is no subsumption relationship between the query concept and the candidate concept.

17. The method according to claim 16, wherein the score for the similarity is calculated between the label of an atomic concept of the query concept and the label of each atomic concept of the candidate concept, and wherein the optimisation is only not performed if all of these scores for the similarity fall below the predetermined threshold.

18. The method according to claim 1, wherein the further comparisons comprises:
determining whether for each relation in the query concept, there is a relation in the candidate concept that subsumes it, and for each concept in the query concept there is a concept in the candidate concept that subsumes it;
if this test returns true, performing further optimisations on the candidate concept;
if this test returns false, performing further optimisations initially on the query concept.

19. The method according to claim 18, wherein after the further optimisation has been performed for either the query concept or the candidate concept, it is again checked whether there is a subsumption relationship; if no subsumption relationship is identified then further optimisation is performed on the other concept.

20. A method of checking whether two concepts defined by a knowledge base have a subsumption relationship comprising:
determining if the first concept of the query concept is subsumed by the first concept of the candidate concept;
determining whether for each relation in the query concept, there is a relation in the candidate concept that subsumes it, and for each concept in the query concept there is a concept in the candidate concept that subsumes it;
choosing an axiom from the knowledge base with a structure: concept-relation-concept, wherein the first concept of the axiom corresponds to a concept from the query concept;
using the axiom in place of the concept from the query concept when checking the subsumption relationship; and
outputting a response to a query based on the determined subsumption relationship.

21. A non-transitory computer readable storage medium including instructions that, when executed by a processor, case the processor to perform the method of claim 1.

22. A text processing apparatus for improving the accuracy of a response to a query directed to a system comprising concepts and relations defined by a knowledge base, wherein the apparatus comprises a processor adapted to:
produce a dependency tree from the query, wherein the dependency tree has at least one branch containing nodes and at least one connection between those nodes, wherein each node has a node label which corresponds to a term within the query, and wherein each connection has a label which corresponds to the linguistic relationship between terms within the query;
from the dependency tree, generate a query concept using concepts and relations defined by the knowledge base;
check if the query concept has a subsumption relationship with a candidate concept retrieved from the system, and if no subsumption relationship is initially identified, optimise the dependency tree by changing the nodes, followed by repeating the generate and the check wherein the query concept and the candidate concept comprise at least one atomic concept; and
outputting the response to the query based on the dependency tree and the query concept.

* * * * *